United States Patent
Manns et al.

(10) Patent No.: US 10,219,690 B2
(45) Date of Patent: Mar. 5, 2019

(54) OPHTHALMIC REFRACTOR AND METHOD OF OPHTHALMIC REFRACTOR SIGNAL ANALYSIS

(75) Inventors: Fabrice Manns, Miami, FL (US); Manuel Bacci, Rubiera (IT); David Borja, Miami, FL (US); Stephanie Delgado, Miami, FL (US); Jean-Marie Parel, Miami, FL (US); Arthur Ho, Sydney (AU); Richard Allen Shelby, Creve Coeur, MO (US); Lutz Andersohn, Glencoe, MO (US); Andres Bernal, Sunny Isles Beach, FL (US)

(73) Assignee: Adventus Technologies, Inc., Irvine, CA (US)

(*) Notice: Subject to any disclaimer, the term of this patent is extended or adjusted under 35 U.S.C. 154(b) by 956 days.

(21) Appl. No.: 13/420,490

(22) Filed: Mar. 14, 2012

(65) Prior Publication Data

US 2012/0238904 A1 Sep. 20, 2012

Related U.S. Application Data

(60) Provisional application No. 61/453,090, filed on Mar. 15, 2011.

(51) Int. Cl.
*A61B 3/10* (2006.01)
*A61B 3/103* (2006.01)
*A61B 3/107* (2006.01)

(52) U.S. Cl.
CPC .......... *A61B 3/1015* (2013.01); *A61B 3/103* (2013.01); *A61B 3/107* (2013.01)

(58) Field of Classification Search
CPC ......... A61B 3/10; A61B 3/103; A61B 3/1015; A61B 3/1035
USPC ........................................... 600/558
See application file for complete search history.

(56) References Cited

U.S. PATENT DOCUMENTS

| | | | |
|---|---|---|---|
| 6,406,146 B1* | 6/2002 | Lai | 351/206 |
| 6,460,997 B1* | 10/2002 | Frey | A61B 3/1015 351/211 |
| 6,736,510 B1 | 5/2004 | Van Heugten | |
| 7,883,505 B2 | 2/2011 | Van Heugten et al. | |
| 7,988,291 B2 | 8/2011 | Ianchulev | |
| 8,342,688 B1* | 1/2013 | Swinger | 351/221 |
| 2012/0026466 A1* | 2/2012 | Zhou | A61B 3/1015 351/214 |
| 2012/0267510 A1* | 10/2012 | Gross et al. | 250/201.9 |

(Continued)

OTHER PUBLICATIONS

Beverage, J. L., "A Shack-Hartmann-Based Autorefractor," Journal of Refractive Surgery, vol. 22, Nov. 2006, 6 pgs.

(Continued)

*Primary Examiner* — Adam J Eiseman
(74) *Attorney, Agent, or Firm* — Jones Day

(57) ABSTRACT

An ophthalmic refractor is described that provides a non-linear relationship between spherical power and refractive error by positioning a reference plane for a sensor system of the refractor in front of the cornea. The refractor may have a working distance and dynamic range that enable it to be mounted on a surgical microscope. Also described are computational methods for analysing the output from the ophthalmic refractor, utilising error minimisation, linear regression and Fourier Transform analysis.

20 Claims, 21 Drawing Sheets

(56) References Cited

U.S. PATENT DOCUMENTS

2014/0300868 A1* 10/2014 Zhou .......................... 351/221

OTHER PUBLICATIONS

Carmon, Y., "Phase retrieval by demodulation of a Hartmann-Shack sensor," Optics Communications 215 (2003), 4 pgs. Available online at www.sciencedirect.com.

Sarver, E. J., "Extracting Wavefront Error From Shack-Hartmann Images Using Spatial Demodulation," Journal of Refractive Surgery, vol. 22, Nov. 2006, 5 pgs.

* cited by examiner

OPHTHALMIC REFRACTOR AND METHOD OF OPHTHALMIC REFRACTOR SIGNAL ANALYSIS

This application claims the benefit of U.S. Provisional Patent Application No. 61/453,090, filed Mar. 15, 2011, which is incorporated by reference herein in its entirety.

FIELD

The disclosed embodiments relate to the fields of: ophthalmic refractors, the mounting of ophthalmic refractor components, methods of measuring ophthalmic refractive error, methods of analysing data from an ophthalmic refractor, apparatus for processing ophthalmic refractor measurements, software, hardware and computer readable media for processing ophthalmic refractor measurements, and methods of performing ophthalmic surgery.

BACKGROUND

Ophthalmic refractors are used to measure ocular refractive error (sphere and cylinder). There are various forms of refractor suitable for measuring ocular refractive error; one form uses a device originally designed to measure ocular aberrations, and is called a Hartmann-Shack aberrometer.

A Hartmann-Shack aberrometer typically measures ocular wavefront aberrations by delivering a parallel beam of near-infrared radiation to the eye. A Hartmann-Shack wavefront sensor is positioned to receive the wavefront leaving the eye. This wavefront sensor includes a relay system, lenslet array and image sensor, which may be a charge-coupled device (CCD), a CMOS sensor, or a video camera. The position of the received infrared radiation on the image sensor the extent of wavefront aberration.

The relay system of a Hartmann-Shack wavefront sensor is an afocal (telescopic) system of two lenses which images a reference plane coincident with the pupil plane onto the lenslet array, typically with a unit magnification (1×). Using this approach, the wavefront curvature at the lenslet array is equal to the wavefront curvature in the pupil plane. The lenslet array is conjugate to the pupil plane and the image sensor is conjugate to the retinal plane.

A Hartmann-Shack wavefront sensor of the type described above has a relay system with a total length of four times the focal length. This long optical path can limit or constrain the uses to which the aberrometer can be put, or at least reduce the convenience of use.

SUMMARY

Embodiments of the invention generally relate to an ophthalmic refractor that provides a non-linear relationship between wavefront spherical power, S, and refractive error, R, by positioning a reference plane for a sensor system of the refractor in front of the cornea. The non-linear relationship may be substantially linear around emmetropia, with the non-linearity increasing at higher refractive errors, both myopic and hyperopic.

The non-linear relationship facilitates a working distance of the refractor of between about 175 mm to about 250 mm. Accordingly, the refractor may be mounted onto or integrated into an operation microscope. The reference plane may be 100 mm or less from the anterior cornea while still providing a useful dynamic range.

In some embodiments the ophthalmic refractor includes a sensor system comprising a lenslet array and a light detector, the lenslet array focussing light onto the light detector; and a relay lens system disposed along an optical path of a return beam of light between the sensor system and a location for the anterior cornea of a subject eye. The relay lens system images the reference plane onto the lenslet array.

The ophthalmic refractor may further comprise a base for mounting one or more of the optical components.

The relay lens system may be part of a beam relay system, which includes a dichroic mirror. The dichroic mirror may protrude at least partially through the base thereby reducing at least one dimension of the ophthalmic refractor, for example the height.

The relay lens system may interface with an operation microscope, the microscope having a central sagittal plane. The relay component may be configured so that an optical axis of the ophthalmic refractor is at 45 degrees from the central sagittal plane of the microscope.

The ophthalmic refractor may further comprise a mounting interface with the microscope comprising a reconfigurable mounting assembly for optical alignment between the ophthalmic refractor and the microscope.

Other embodiments of the invention generally relate to a method for measuring ophthalmic refractive error. The method includes directing onto a Hartmann-Shack sensor system the wavefront of a return light beam from a subject eye, which wavefront is been referenced at a location in front of the cornea, so as to provide a non-linear relationship between spherical power and refractive error. The method may further include using a relay system to offset the sphere to refractive error relationship.

Other embodiments of the invention generally relate to methods of analysing wavefront data generated by a Hartmann-Shack sensor system with a non-linear relationship between spherical power and refractive error. The methods include: in a computational system performing a linear regression on centroid positions of spots defined by the wavefront data; running an error minimisation algorithm to find coefficients of a function defining the difference in position between centroids of spots defined by the wavefront data and reference centroid positions; and computing a frequency domain transformation of the wavefront data and computing a solution to an equation relating the centroid position of the transformed wavefront data to one of the following vectors:

spherical power (S) only;
S and cylindrical power (C);
S, C and axis angle, $\alpha$;
Cross-cylinder format (involving two cross cylindrical powers C1 and C2);
mean spherical power (M) only;
M and astigmatic power (J);
M and astigmatic power vectors ($J_0$, or $J_0$ and $J_{180}$);
M, J and $\alpha$;
M and $J_0$ and $J_{45}$.
The detailed description provides examples of calculations/computations to a subset of the vectors. Other vectors may be calculated/computed using known mathematical relationships between light received by a Hartmann-Shack sensor system and these other vectors and/or through known mathematical relationships between the aforementioned vectors.

Other embodiments of the invention generally relate to a method of performing an ophthalmic surgical procedure on a subject eye. The method includes using a refractor with a non-linear relationship between spherical power and refractive error. The surgeon may act responsive to an output of the refractor to achieve a target refractive error.

DETAILED DESCRIPTION

Figure 1:
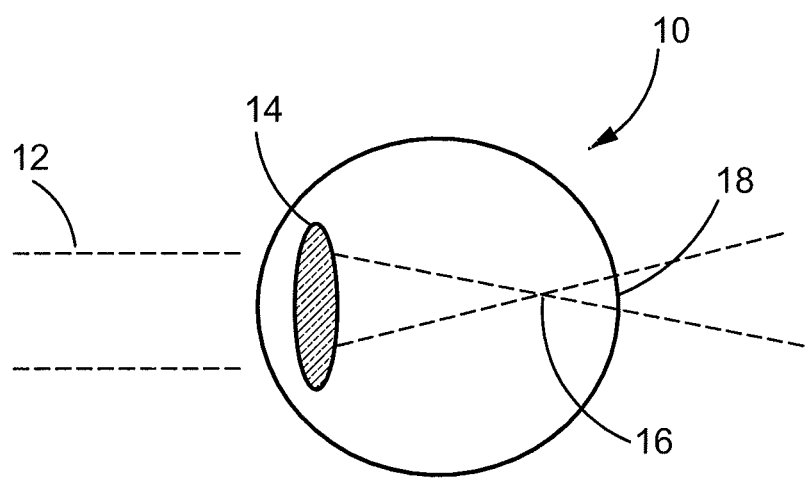
FIG. 1: shows a schematic representation of an eye exhibiting myopia.

FIG. 1 is a schematic representation of an eye 10 exhibiting myopia: collimated light 12 is focused by the unaccommodated lens 14 of the eye at a position 16 in front of the retina 18, instead of on the retina.

Figure 2:
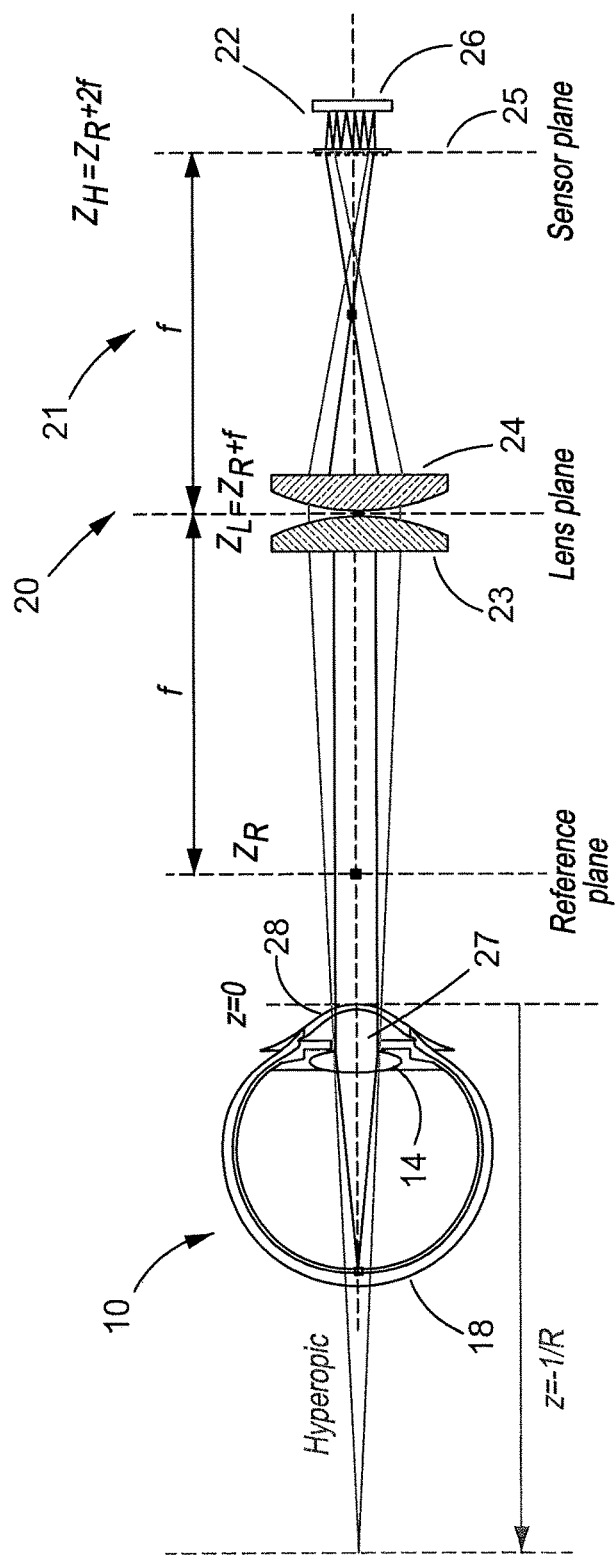
FIG. 2: shows a diagrammatic representation of optical components of an ophthalmic refractor with a reference plane in front of the anterior cornea of a subject eye.

FIG. 2 shows a diagrammatic representation of a refractor according to embodiments of the present invention. For the purposes of clarity of illustration the source of the infrared or other radiation to be measured and its optical path onto the retina has been omitted from FIG. 2 and instead only the optical path of the return beam from the retina to the refractor is shown.

The refractor 20, includes a relay system 21 and a sensor system 22 for sensing a wavefront from the relay system 21. The relay system 21, in this embodiment comprises a first plano-convex lens 23 and a second plano-convex lens 24, which are located about a lens plane $Z_L$. The sensor system 22 includes a lenslet array 25 positioned at plane $Z_H$ and a charge coupled device (CCD) 26. In alternative embodiments the CCD may be omitted and replaced with a CMOS sensor, video camera or other suitable image sensor. The refractor 20 is shown with its optical measurement path aligned with a subject eye 10. Shown in FIG. 2 is the retina 18, lens capsule 14, pupil 27 and cornea 28. FIG. 2 also shows a base position Z=0, designated as the position from which the optical location of the components of the refractor 20 is measured. In FIG. 2 Z=0 is the position of the anterior cornea.

In this embodiment, the lenses 23, 24 have the same focal length f. Accordingly, the lens plane $Z_L$ is at $Z_R$+f and the lenslet plane $Z_H$ is located at $Z_R$+2f, where the relay system 21 images the wavefront from the retina reflection at a reference position $Z_R$, located anterior to the cornea (which is designated distance zero Z=0). The image magnification, in this embodiment, is m=−1. Using this arrangement, the relation between the spherical power S measured in dioptres D at the sensor system 22, the refractive error R of the subject eye 10, the reference position $Z_R$ and the power P of the relay system 21 is described by equation 1.

$$S = \frac{R}{1 + R \cdot Z_R} + P. \qquad \text{equation 1}$$

Accordingly, the design parameters of the refractor 20 include the power P of the relay system and the reference position $Z_R$ (being the distance from Z=0 to $Z_R$). The power P is 2/f, where f is the focal length of each of the plano-convex lenses 23, 24.

In some embodiments, the refractor 20 may be an operation microscope mounted refractor. In these embodiments, the required working distance w of the refractor 20 may be at least as large as the focal length of the operation microscope. A typical operation microscope may have a working distance of about 175 mm. Additional clearance may be required to leave room to mount other optical components, for example one or more beam splitters to allow other measurement or monitoring to take place. Accordingly, the refractor 20 may have a design constraint of a working distance of about 200 mm. The working distance w is the sum of the focal length of the lenses 23, 24 with the reference plane $Z_R$ (w=f+$Z_R$). In other embodiments, for example if the refractor was to be implemented as a hand-held refractor, the working distance may be similar to that required for mounting on an operation microscope, or greater or lesser.

According to equation 1 there is a singularity (S is infinite) when R=−1/$Z_R$. Accordingly, to avoid exceeding the dynamic range of the sensor system 22, the refractive error must be larger (less myopic) than −1/$Z_R$. For example, if the desired myopic measurement range is −10D then the value of $Z_R$ must remain below approximately 100 mm.

Figure 3A:
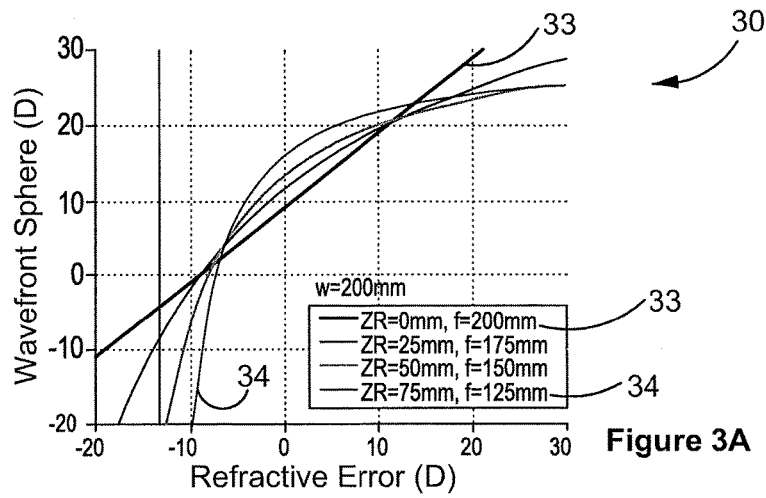
FIGS. 3A-C: show graphs of the spherical power versus refractive error according to a model of the refractor shown in FIG. 2, each graph associated with a different working distance, w.
Figure 3B:
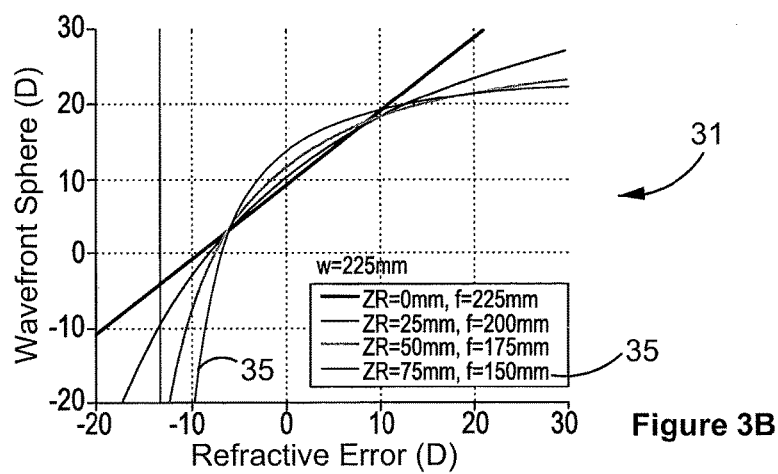
Figure 3C:
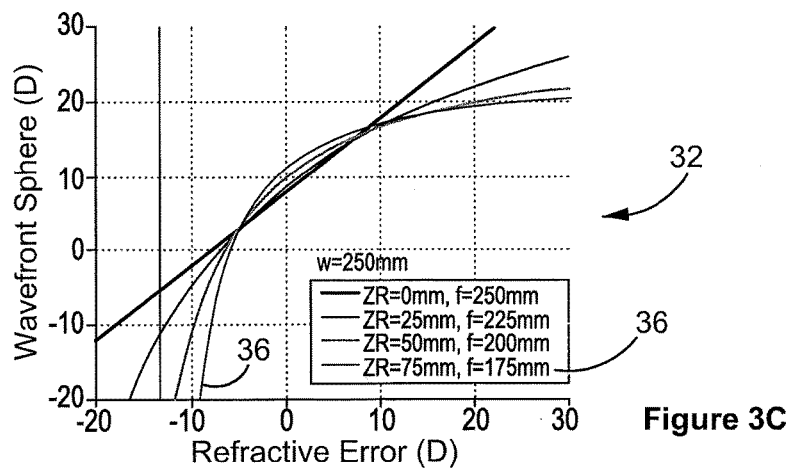

FIG. 3A shows a graph 30 of the spherical power S versus refractive error R according to the model of equation 1 for a working distance of w=200 mm. FIG. 3B shows a graph 31 of the spherical power versus refractive error according to the model of equation 1 for a working distance of w=225 mm. FIG. 3C shows a graph 32 of the spherical power versus refractive error according to the model of equation 1 for a working distance of w=250 mm. Each graph shows four plots of spherical power (which is referred to as 'wavefront sphere' in these figures) versus refractive error, for four different focal lengths of the relay system 21. The corresponding reference position $Z_R$ for each focal length is also indicated in the legend to each graph. (The legends and graphs shown have corresponding reference numerals, for example in graph 30, curve 33 indicates the spherical power S for $Z_R$=0 mm and f=200 mm, and in graph 31 curve 35 indicates the spherical power S for $Z_R$=75 mm and f=150 mm).

When the reference position $Z_R$ is the corneal plane ($Z_R$=0), the spherical power is equal to the refractive error plus the power of the relay system (2/f). In hyperopic eyes, the spherical power increases at a slower rate as the refractive error increases when $Z_R$>0 than when $Z_R$=0. In myopic eyes, the spherical power increases at a faster rate as the refractive error increases when $Z_R$>0 than when $Z_R$=0. In other words, shifting the reference plane anterior to the cornea ($Z_R$>0) produces a non-linear (or curvilinear) relationship. This non-linear relationship helps to increase the hyperopic range of the refractor, but decreases the myopic range. For example, if it is assumed that the wavefront sensor has a dynamic range of −20D to +20D of sphere and that the working distance is 225 mm, the measurement range will be −29D to +11D for $Z_R$=0 mm, −17D to +13.5D for $Z_R$=25 mm, −12D to +15D for $Z_R$=50 mm, −9.5D to +13.5D for $Z_R$=75 mm.

Accordingly, the refractor may be designed to operate or may be operated with a reference position $Z_R$ within 75 mm≥$Z_R$>0 mm. In other embodiments, the range may be 50 mm≥$Z_R$>0 mm. In other embodiments, the range may be 25 mm≥$Z_R$>0 mm. In other embodiments, the range may be 25 mm≥$Z_R$>10 mm. In other embodiments, the range may be 25 mm≥$Z_R$>15 mm. Adopting a reference value of 25 mm or 50 mm for working distances w of 200 mm, 225 mm and 250 mm gives the parameters shown in Table 1 for the refractor 20. In Table 1 all measurements are expressed in millimeters, w is the working distance, $Z_R$ is the reference position and f is the focal length of the relay system 21.

TABLE 1 example refractor parameters

| w (mm) | 200 | 200 | 225 | 225 | 250 | 250 |
|---|---|---|---|---|---|---|
| $Z_R$ (mm) | 25 | 50 | 25 | 50 | 25 | 50 |
| f (mm) | 175 | 150 | 200 | 175 | 225 | 200 |

Another design parameter is the diameter of the beam leaving the eye and reaching the lenslet array 25. The beam diameter must be large enough to cover a few lenslets, for example to have a diameter of about 4 times the pitch of the lenslet array or more. On the other hand, if the beam is much larger than the entire lenslet array, the variation of the ray slope over the lenslet array may be below the sensitivity of the sensor system 22.

Assuming that the relay system 21 images the reference position $Z_R$ onto the lenslet array with unity magnification, in other words m=−1, then the beam diameter, $d_H$ (in meters), is related to the pupil diameter, $d_P$ (in meters), the reference position $Z_R$ (in meters) and refractive error R (in dioptres) by equation 2.

$$d_H = d_P \cdot (1 + R \cdot Z_R)$$ equation 2.

Figure 4:
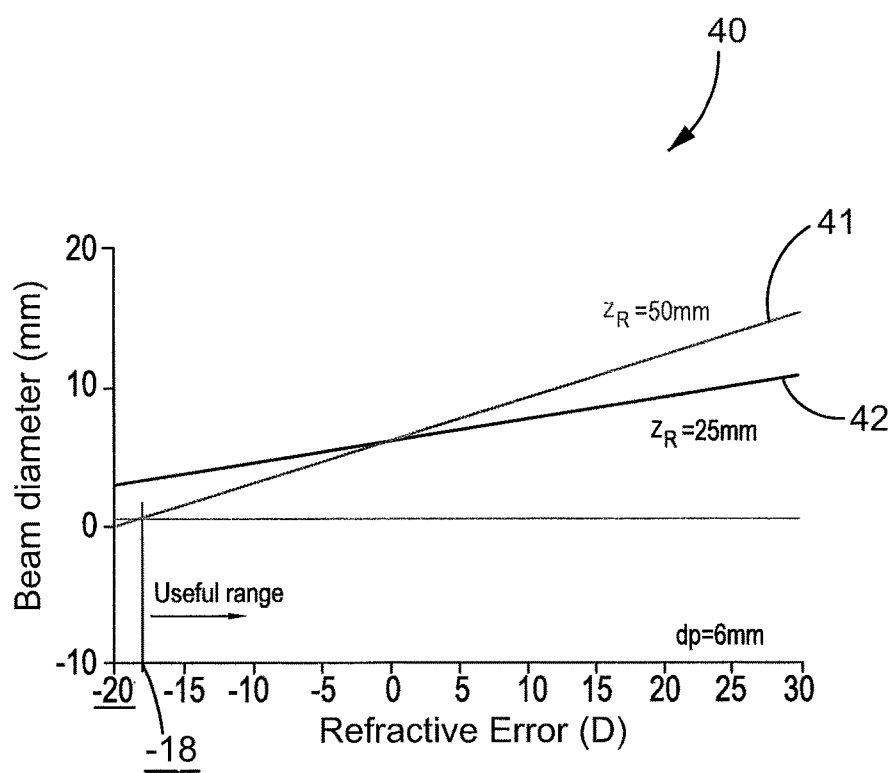
FIG. 4: shows a graph representing a relation between beam diameter and refractive error in a refractor of the type shown in FIG. 2.

FIG. 4 shows a graph 40 of the beam diameter as a function of the refractive error for a reference position $Z_R$=50 mm (41) and for a reference position $Z_R$=25 mm (42). The pupil diameter $d_P$=6 mm for this example. With a 0.15 mm lenslet pitch, the measurement range is more than −20D for a reference position of 25 mm and −18D for a reference position of 50 mm.

By way of example, if the objective is a minimum beam diameter of 4 times the pitch of the lenslet array and the pitch is assumed to be 0.15 mm, then setting $d_H$>0.6 mm in equation 2 gives a maximum myopic error of −9.0D for a working distance of 100 mm and −4.5D for a working distance of 200 mm.

1. Testing of the Model

A test system was assembled on an optical table, using the following components:

A relay lens doublet consisting of 2 identical plano-convex lenses (f=150 mm or f=175 mm)

A Hartmann-Shack wavefront sensor (Part number WFS 150-7AR, sourced from Thorlabs).

A fiber-coupled superluminescent diode (Part number SLD2371, 3 mW, 830 nm, sourced from SuperLum).

A collimator assembly (0.86 mm beam diameter, part number OFR PAF-X-5-B, sourced from Thorlabs).

An eye model consisting of an f=15 mm plano-convex lens and a mirror mounted on a translation stage near the lens focus.

A pellicle beam splitter (2", part number BP245B2, sourced from Thorlabs).

Figure 5:
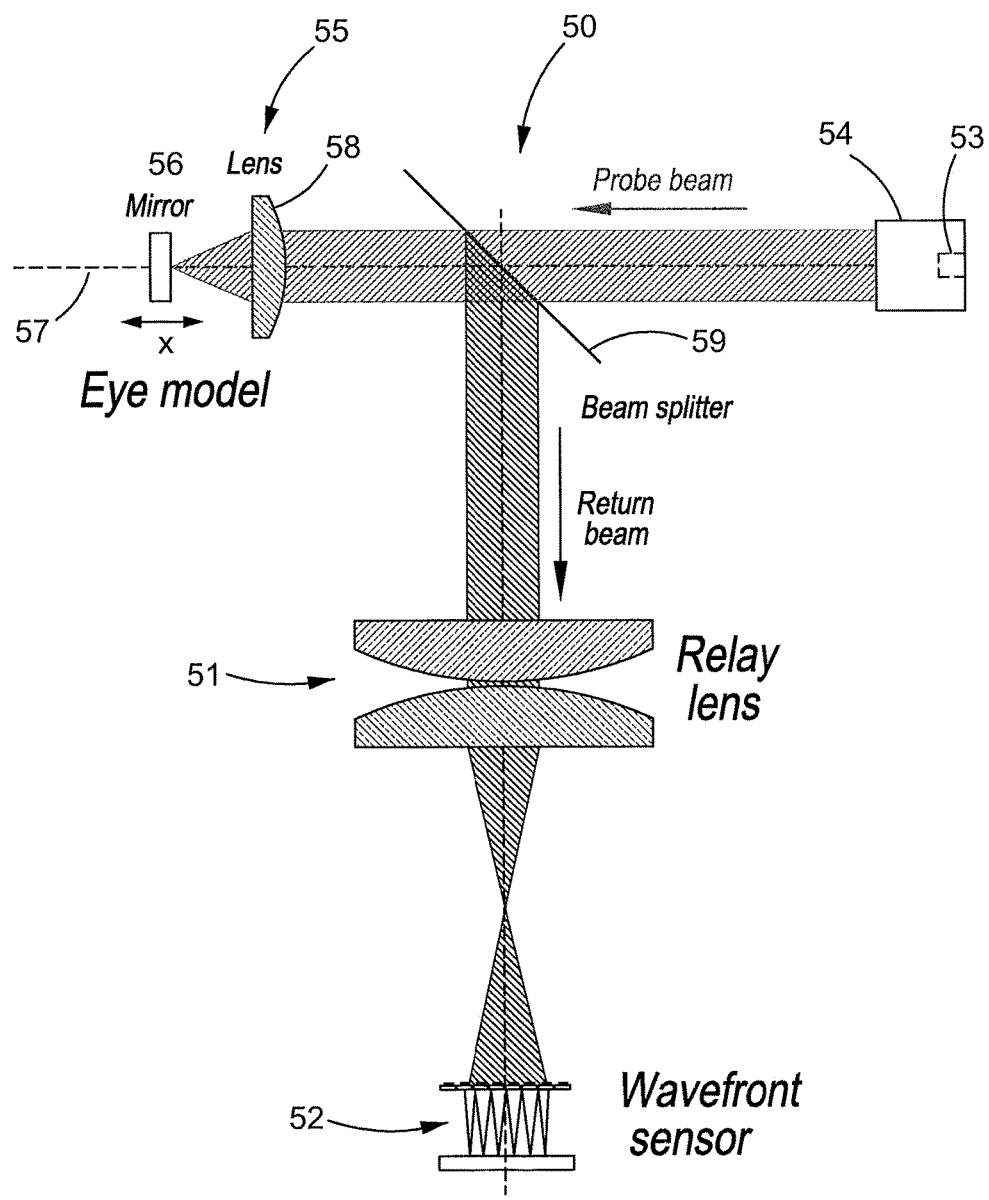
FIG. 5: shows a diagrammatic representation of a test refractor with a reference plane in front of the anterior cornea of a model eye.

FIG. 5 shows a representation of the test system refractor 50. In FIG. 5, the relay lens doublet is referenced 51, the Hartmann-Shack wavefront sensor is referenced 52, the fiber-coupled superluminescent diode (SLD) is referenced 53, the collimator assembly is referenced 54, the eye model is referenced 55 and the pellicle beam splitter is referenced 59. The test system refractor 50 has a like measurement optical structure to that shown in FIG. 2. In addition, the test system refractor 50 includes the light source. As such it has a general physical structure suitable for reproduction, for example, in a surgical microscope mounted refractor.

The refractive error of the eye model 55 was adjusted by translating the mirror 56 along the optical axis 57 of the lens 58. The eye model is emmetropic when the mirror 56 is located at the focal plane of the lens 58. From this reference position, the eye model is made hyperopic by moving the mirror 56 towards the lens 58. It is made myopic by moving the mirror 56 away from the lens 58. For this eye model 55, the relation between the refractive error of the eye model, R, the focal length of the lens, $f_e$, and the displacement of the mirror from the emmetropic position, x, is given by equation 3.

$$R = -\frac{1}{f_e} + \frac{1}{f_e + 2 \cdot x}.$$ equation 3

The factor 2 in equation 3 is present because the mirror 56 produces a virtual image of the focal point of the lens. A displacement x of the mirror 56 from the emmetropic position produces a displacement 2x of the final virtual image, which corresponds to the retina of the eye model.

1.1. Experiments

Calibration experiments were conducted with a working distance of w=225 mm for the following two sets of parameters: f=150 mm, $Z_R$=75 mm and f=175 mm, $Z_R$=50 mm. The goals of this experiment were:
- to verify that the experimental system behaves as predicted by the theory (Equation 1);
- to provide an estimate of the dynamic range and sensitivity of the design.

Figure 6A:
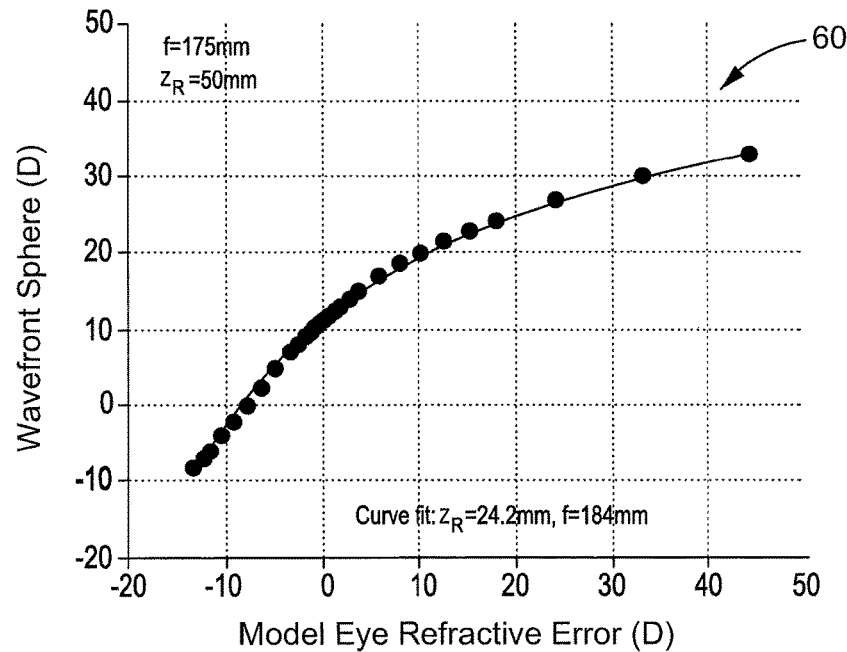
FIGS. 6a, 6b: show graphs comparing spherical power against refractive error obtained from the test refractor represented in FIG. 5 against the values indicated by a mathematical model of the refractor.
Figure 6B:
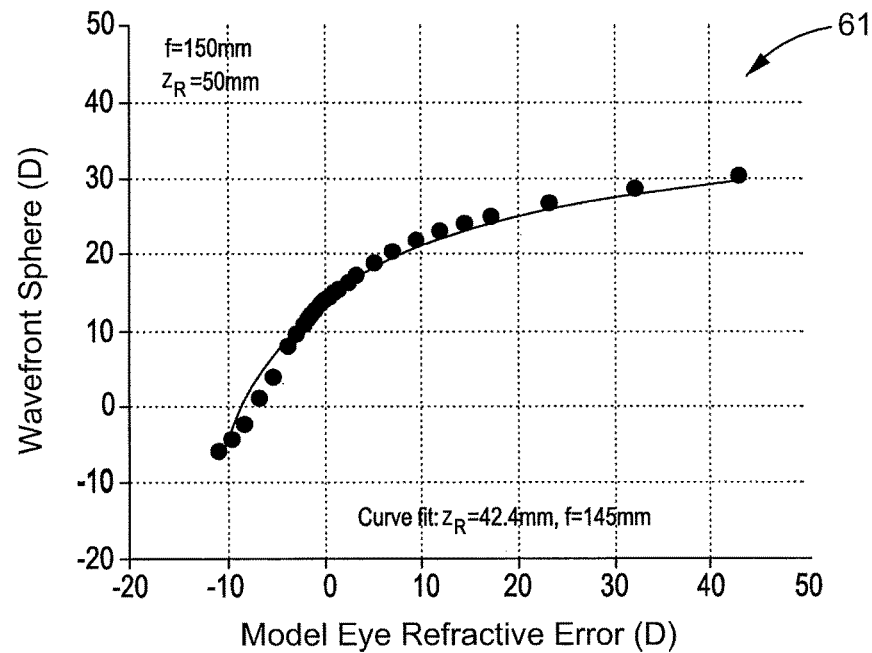

FIG. 6A shows a curve 60 of the spherical power S as a function of refractive error R for a test system with f=175 mm and $Z_R$=50 mm. FIG. 6b shows a curve 61 of the spherical power S as a function of refractive error R for a test system with f=150 mm and $Z_R$=75 mm. In these figures, the dots represent experimental data (spherical power, in diopters (D)) and the continuous lines are curve fits using either the theoretical equation (FIG. 6A) or a non-linear approximation (FIG. 6B).

The results of FIGS. 6A, 6B show that the experimental outcomes are in good agreement with the theoretical predictions. The differences are within expected experimental error and result, amongst others, from certain assumptions made in the model such as a focal length of 15 mm for the lens of the eye.

The measurement range in all experiments was from less than −10D to more than +40D. In the range of refractive errors near emmetropia (−2D to +2D), the spherical power (S) varies linearly with refractive error (R), as was apparent from the experimental results and as predicted from a Taylor series approximation of equation 1, which gives S=R+P, when R is small. In this region, the sensitivity is approximately 0.15D.

The theoretical analysis and experiments show that, with the parameters and components used in the benchtop prototype:
- The proposed design using a relay lens and shift of the reference plane is expected to provide a useful dynamic range (at least −10D to +30D) with a useful sensitivity of about +/−0.15D near emmetropia.
- The effect of the relay lens is to offset the spherical power by an amount equal to the dioptric power of the relay system.
- Shifting the reference plane away from the cornea introduces a non-linearity for large refractive errors. The non-linearity helps increase the hyperopic measurement range.
- Near emmetropia, the spherical power versus refractive error response is linear with a slope of +1.

In this arrangement the response is non-linear away from emmetropia so that the dynamic range is asymmetrical. The longer dynamic range is to the hyperopia (positive) refractive error direction. This may result in advantages in lens refilling applications (such as in the phace ersatz technique), since during the procedure, the lens is extracted (i.e. goes from about 20D to about 0D), which renders the eye approximately 20D hypermetropic. In some embodiments, the asymmetry producing a greater dynamic range in the positive side may keep the measurement within range even during lens extraction.

Figure 7:
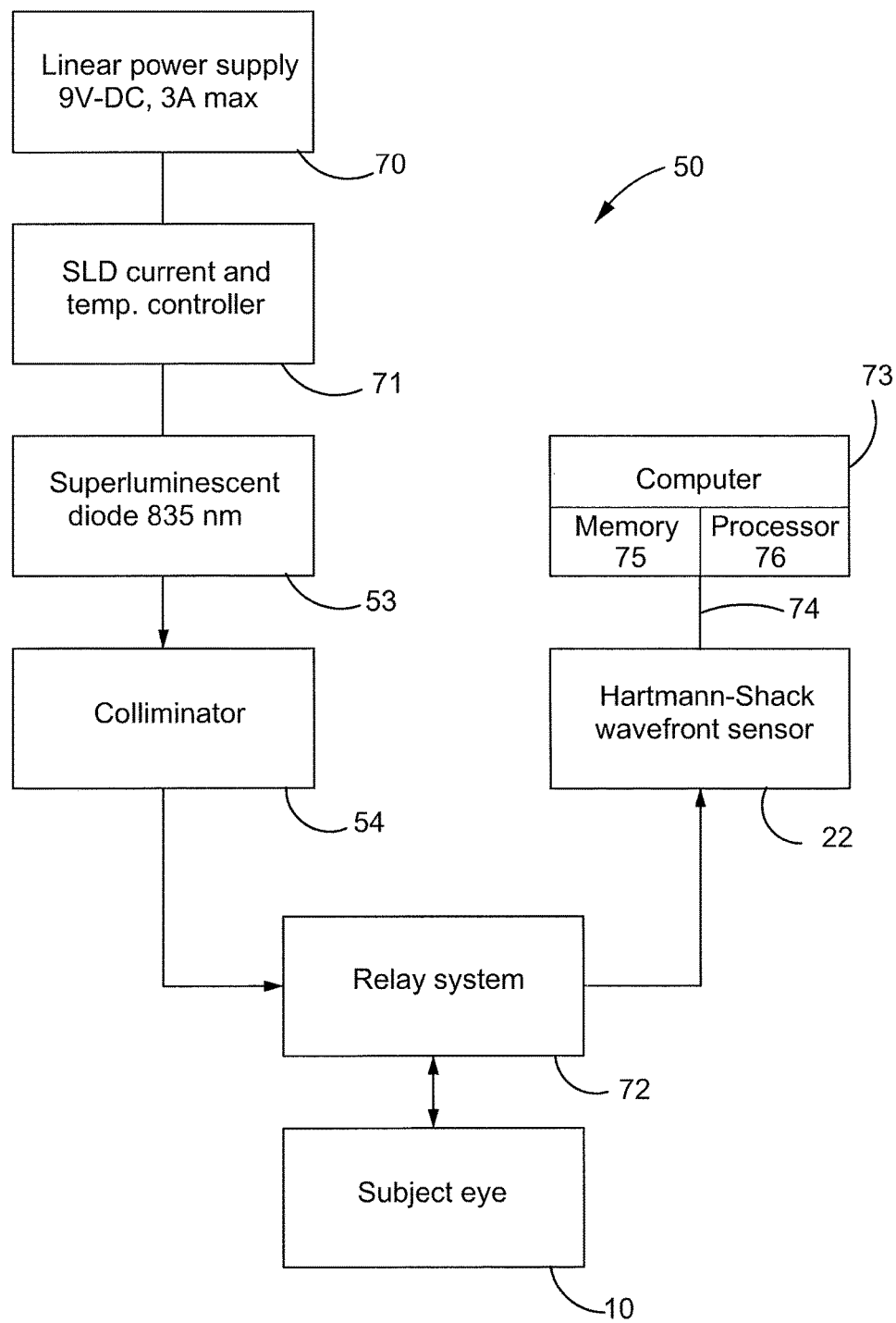
FIG. 7: shows a block diagram of an ophthalmic refractor.

FIG. 7 shows a block diagram of a refractor 50 of the type described with reference to FIGS. 2 and 5, together with a block representation of a subject eye for measurement. Like reference numerals between FIG. 7 and FIGS. 2 and 5 represent like components. The refractor 50 includes a power supply 70, in this embodiment a linear power supply of 9V-DC with a maximum current of 3A. The power supply 70 provides power to a superluminescent diode (SLD) current driver and temperature controller 71, which in turn controls the current through the fiber-coupled superluminescent diode 53. Light from the diode 53 is collimated into a beam by the collimator 54 into the required beam diameter (see the description herein above with reference to FIG. 4). This beam is directed onto the retina of the subject eye 10 and the return beam received through a beam relay system 72. As described in relation to FIG. 5, the beam relay system 72 may include a beam splitter 59 and a relay lens system 51.

The return beam from the subject eye 10 is received by the sensor system 22, a Hartmann-Shack Wavefront Sensor. The sensor system 22 outputs the detected spots resulting from the return beam as a data signal to a computer 73. In the embodiment, the data is communicated through USB ports and a USB cable 74. The computer 73 includes in memory 75 software including instructions to cause the computer's processor 76 to, at least, determine the refractive error of the eye. Suitable software to achieve this is available, for example from Thorlabs for use with the Thorlabs WFS-150-5c sensor. Alternatively, the software may execute one or more algorithms described herein, for example through a custom program or through a math program, for example MATLAB, in which the algorithms have been entered.

Figure 8:
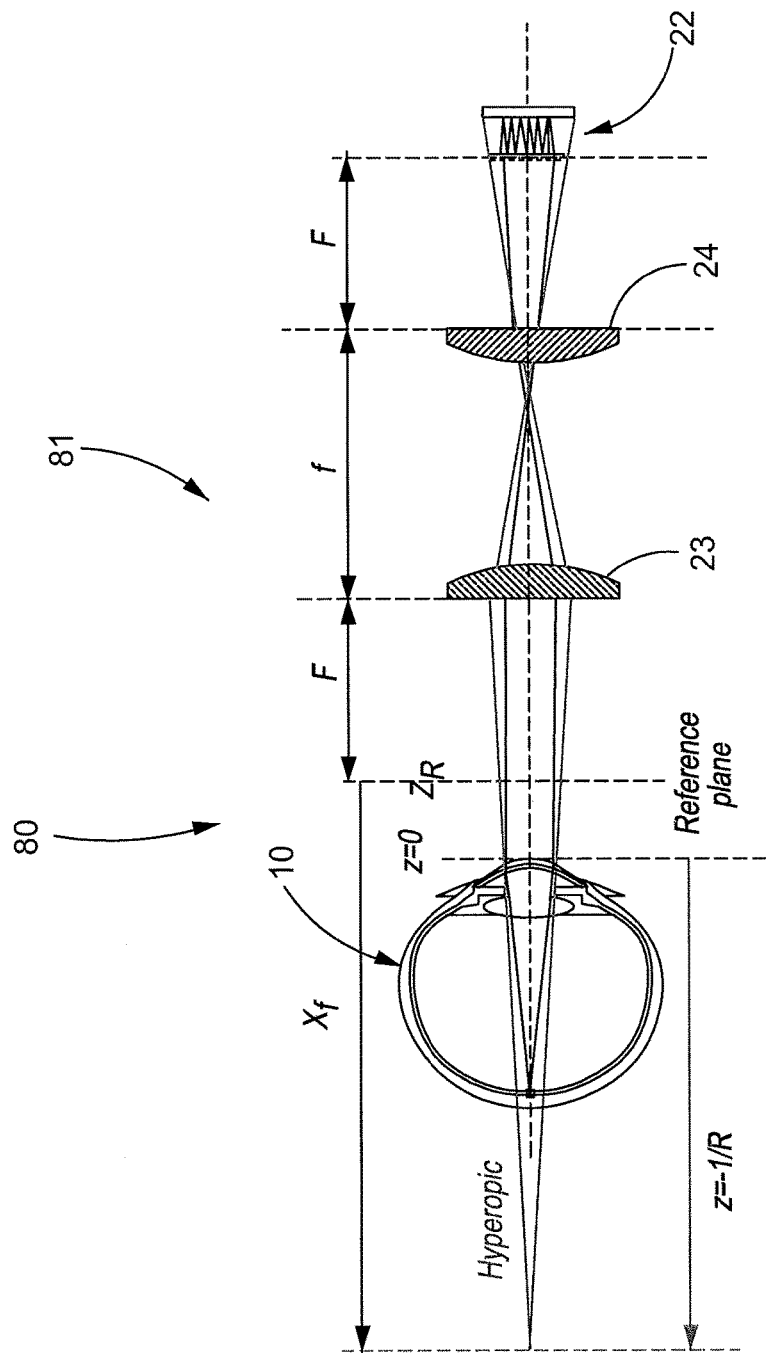
FIG. 8: shows a diagrammatic representation of optical components of another embodiment of an ophthalmic refractor with a reference plane in front of the anterior cornea of a subject eye.

2. Relay System with Different lens Separations and Alternative Relay Systems FIG. 8 shows a more generalised representation of a refractor 80, which includes a variable parameter relay system 81. The relay system 81, is similar to the relay system 21, and like reference numerals between the two figures reference like components. The refractor 80 has an additional design parameter of the distance between the plano-convex lenses 23, 24. This parameter is referenced t in FIG. 8. Where t=0, then FIG. 8 is equivalent to FIG. 2. When t=2f, with f again being the focal length of the lenses 23, 24, then the relay system 81 is telescopic. As shown in FIG. 8 both lenses 23, 24 have the same power. The effect of lenses with differing powers is discussed herein below.

Using this arrangement, the relation between the spherical power S measured at the sensor system 22, the refractive error R, the reference position $Z_R$ is described by equation 4. In equation 4, k is the separation of the lenses 23, 24 relative to 2f so k=t/2f $$S = \frac{R}{1 + R \cdot Z_R} + \frac{2 \cdot (1-k)}{f}. \qquad \text{equation 4}$$

Equation 4 shows that the wavefront curvature includes an offset when compared to a telescopic relay system (t=2f), the magnitude of the offset being dependent on the focal length and distance between the two lenses in the relay system 21. The offset is the value of the spherical power when the refractive error is equal to zero. The offset is equal to zero when the system is telescopic (k=1) and equal to 2/f when the two lenses are in contact (k=0).

Table 2 provides values of the wavefront curvature offset introduced by the relay system for f=100 mm and f=200 mm. The table shows that a larger value of k also implies a longer system.

TABLE 2

| | wavefront curvature offset | |
|---|---|---|
| | f = 100 mm | f = 200 mm |
| k = 0 | 20 D | 10 D |
| k = 0.25 | 15 D | 7.5 D |
| k = 0.5 | 10 D | 5 D |
| k = 0.75 | 5 D | 2.5 D |
| k = 1 | 0 D | 0 D |
| k = 1.25 | −5 D | −2.5 D |
| k = 1.5 | −10 D | −5 D |

Referring to FIGS. 3a to 3c, the offset from Table 2 is zeroed for k=0 and added to the wavefront curvature to obtain the value for spherical power. For example, for f=200 mm if it is assumed that the wavefront sensor has a dynamic range of −20D to +20D of sphere and that the working distance is 225 mm ($Z_R$=25 mm), the measurement range will be −17D to +13.5D for k=0, and −9.5D to +21D for k=0.25.

Referring to FIGS. 3A-C, the value of the reference position $Z_R$ (which determines the non-linearity) and the power of the relay system (which determines the offset) can be altered to optimise the non-linear response to provide the desired dynamic range. Referring to FIG. 3A, the offset ranges from 2/0.2=10D when f=200 mm to 2/0.125=16D when f=125 mm. If there would be no offset, then all the curves in FIG. 3A would be shifted down by 10 to 16D. This would reduce the myopic range. On the other hand, the offset decreases the hyperopic dynamic range, since it shifts the curve upward. The downward non-linearity in the hyperopic range compensates for the upward offset.

Alternative relay systems to that described above may be used in other embodiments. The relay lens could be any arrangement of 1, 2 or more lenses in contact or near contact that produces an image of the reference plane on the plane of the lenslet array.

While the preceding description provides an example of a pair of plano-convex lenses of equal focal length that produces a magnification of −1, in alternative embodiments, the focal length of the lenses is mismatched to produce a different magnification. If f1 is the focal length of the lens closest to the eye and f2 is the focal length of the lens closest to the lenslet, the magnification is m=−f2/f1. The value of f1 is also the working distance of the system. For a given working distance, the value of f2 can be selected to produce the desired magnification. The magnification can be adjusted to match the diameter of the desired optical zone in the reference to the diameter of the lenslet array.

Magnification also affects the dynamic range of the refractor. The dynamic range is proportional to the square of the magnification. For instance, a system with a magnification of −0.5× will have a dynamic range that is four times less than a system with a magnification of −1×. Accordingly, in some embodiments a magnification equal to or greater than −1× is selected to increase the measurement range.

In some embodiments, instead of two plano-convex lenses, the lens could also be a biconvex lens, or a best-form singlet lens designed to minimize the aberrations introduced by the relay system. In addition, one or both of the lenses may be achromatic. More complex lens trains may also be used for either or both of the lenses to improve performance and reduce monochromatic or chromatic aberrations.

3. Reference Plane Position and Separation of Lenses

Some embodiments of refractor have a reference plane in front of the cornea and a distance t=2f. Other embodiments of refractor have a reference plane in front of the cornea and a distance 0<t<2f. Other embodiments have a reference plane on the cornea or on the pupil and a distance t<2f.

In some embodiments the reference plane is variable within a range, for example from the cornea outwards. Variability may be achieved by, for example, a mechanical system to vary the location of the relay system along an optical path from the subject eye, or through an electric system, like a servo motor.

The position of the reference plane and/or the distance t (or value k described above) may be an input variable to a computer (see herein) that computes the refractive error. The computer may then compensate for variation of the wavefront dependent on the reference plane position and/or distance t.

4. Example 1—Operation Microscope Mounted Refractor

Figure 9:
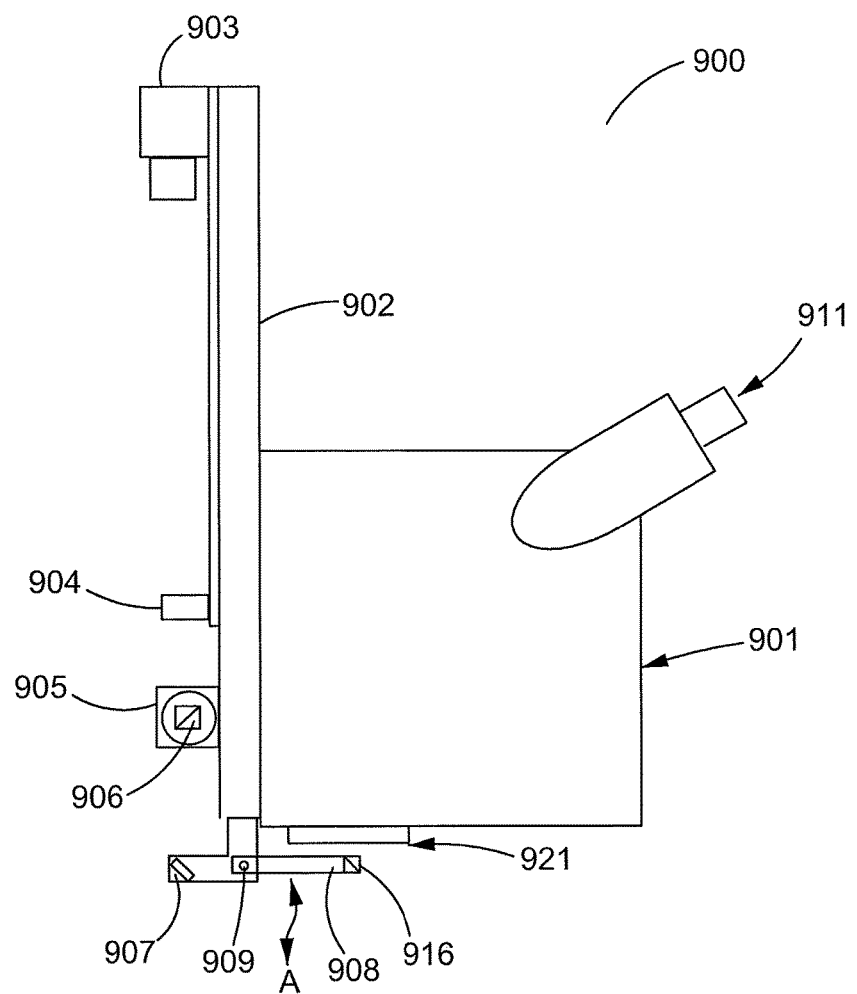
FIG. 9: shows a diagrammatic representation of an operation microscope mounted ophthalmic refractor.

FIG. 9 shows a diagrammatic representation of a microscope and refractor 900. The refractor system mounted to the microscope as shown in FIG. 9 is termed "outside-coupled". The microscope 901 may be an ophthalmic operation microscope, including eye pieces 911 and entrance lens 921. The operation microscope 901 will be mounted on a suitable platform (not shown), for example suspended below a pivoting arm assembly. Operation microscopes are well known and therefore the operation microscope 901 is not further described herein.

A mounting block 902 is secured to the operation microscope 901. The mounting block 902 provides structural support for the components of the refractor. The refractor includes:

a sensor system (22, 52) in the form of a Hartmann-Shack sensor system 903 for receiving the return beam from the subject eye and generating a spot pattern for analysis;

a relay lens system (21, 51), in the form of plano-convex lenses (not visible), for receiving the return beam from the subject eye and imaging it onto a sensor plane of the Hartmann-Shack sensor system 903; the lenses are contained within a housing 904 that maintains the lenses at a fixed separation (which may be zero), the relay lens system providing a reference plane $Z_R$ that is positioned or able to be positioned in front of the cornea of the subject eye;

a light source 905 (53 and 54) that projects an incident beam of light in the direction out of the page and towards the first beam splitter 906;

a first beam splitter 906 to direct an incident beam of light from the light source 905 vertically downwards and to allow the return light beam to travel past it to the relay lens system;

a mirror 907 to receive the incident light beam from the beam splitter 906 and direct it horizontally to the right and to receive the return light beam from the eye and direct it to the first beam splitter 906; and a second beam splitter 916, mounted on a moveable arm 908 that rotates about a pivot 909 to move the beam splitter 916 into and out of the field of view of the entrance lens 921, the beam splitter 916 receiving the incident light beam from the mirror 907 and directing it onto the retina of the subject eye and also receiving the return light beam from the retina and directing it to the mirror 907.

The reference numerals in brackets refer to corresponding components in FIGS. 2 and 5. References to direction are made with reference to the orientation shown in FIG. 7. It will be appreciated that other physical arrangements are possible which may involve different orientations and that the incident light beam and return light may traverse different physical optical paths.

5. Calculation of the Refractive State—General Process

Referring again to FIG. 2, the acquisition of the data from the sensor system 22 and processing of the acquired data are two separate independent steps that can be done with different programs, for example LabView to acquire the data and Matlab to process the data. In other embodiments, these functions are performed under the control of a single program.

The CCD 26 is connected to a USB port or to a video card located inside a computer. Control of the camera acquisition sequence and acquisition of the camera data is done through a computer programming language such as C, MATLAB, LabView or CVI-LabWindows, or equivalent, after installation of software drivers that are provided either by the camera manufacturer or in a library or as an add-on of the programming language. As will be appreciated, the camera software driver facilitates communication and direct data exchange between the computer and the camera.

The data read from the camera is in the form of a data file that contains the intensity recorded by each pixel as well as the camera settings. The file is formatted in the form of a two-dimensional array that will provide a direct correspondence between each array element and a pixel in the camera. Data processing to find the centroid positions or compute the Fourier transform (see below) is performed on this data array, using the same programming language as used for data acquisition.

The centroid positions may be used to determine a number of vectors relating to the refractive state of the subject eye. These may include: spherical power (S) only; S and cylindrical power (C); S, C and axis angle, $\alpha$; Cross-cylinder format (involving two cross cylindrical powers C1 and C2); mean spherical power (M) only; M and astigmatic power (J); M and astigmatic power vectors ($J_0$, or $J_0$ and $J_{180}$); M, J and $\alpha$; and/or M and $J_0$ and $J_{45}$.

6. Calculation of the Refractive State from the Centroid Positions

The lenslet array 25 of the sensor system 22 samples the wavefront and focuses each wavefront sample onto the CCD 26. The CCD 26 is located in the focal plane of the lenslet array. The position of the centroid of each spot is directly related to the wavefront error. If the wavefront reaching the lenslet array 25 is a planar wavefront parallel to the wavefront sensor, the spot centroids are aligned with the centre of the lenslets. In all other cases, spot centroids will be shifted by an amount related to wavefront error.

The following description and equations are given for a wavefront sensor with a square lenslet array, which is a typical form. Further, to simplify the mathematical expressions, it is assumed that the number of rows and columns, N, of the array is an odd number. In alternative embodiments a rectangular lenslet array with any number of lenslets may be used, with suitable modification to the spot pattern analysis. If the lenslet array is an N×N array of lenslets with a pitch p, then adopting a description of the sensor system 22 in the form of a Cartesian coordinate system in the plane of the lenslet array, centred at the centre of the lenslet array, provides the coordinates of the lenslet centres are described by equation 5.

$$(x_m, y_n) = (m \cdot p, n \cdot p) \qquad \text{equation 5.}$$

Where m is an integer representing the column number and n is an integer representing the row number. The centre of the array (m=0 and n=0), has coordinates $x_0=0$, $y_0=0$. If the number of rows and columns, N, of the array is an odd number, then $-(N-1)/2 \leq m, n \leq (N-1)/2$. For an eye with sphere-cylindrical refractive error, the refractive error varies with the meridional angle $\theta$. Using Fourier notation, the variation of sphero-cylindrical refractive error $R(\theta)$ can be expressed as a function of the meridional angle according to equation 6.

$$R(\theta) = M + J_0 \cdot \cos(2\theta) + J_{45} \cdot \sin(2\theta) \qquad \text{equation 6.}$$

M is the mean spherical power and $J_0$ and $J_{45}$ are the powers of cross cylinders with axes at 0° and 90°, and 45° and 135° respectively. The spherical power, S, cylindrical power, C, and axis angle, $\alpha$, of the traditional notation of sphere-cylindrical refractive error, in negative cylinder form, are related to M, $J_0$ and $J_{45}$ through the relations in equation 7.

$$\begin{cases} S = M + \sqrt{J_0^2 + J_{45}^2} \\ C = -2 \cdot \sqrt{J_0^2 + J_{45}^2} \\ \alpha = \frac{1}{2} \cdot \text{Arctan} \frac{J_{45}}{J_0} \end{cases} \quad \begin{cases} M = S + \frac{C}{2} \\ J_0 = -\frac{C}{2} \cdot \cos 2\alpha \\ J_{45} = -\frac{C}{2} \cdot \sin 2\alpha \end{cases} \qquad \text{equation 7}$$

For an eye free of refractive error, the centroids of the spots in the spot distribution received by the image sensor will be located at coordinates $(x_m, y_n)$, corresponding to the centres of the lenslets. In the presence of refractive error, the centroids will be displaced. In the following description, the coordinates of the displaced centroids corresponding to the lenslet centred at coordinates $(x_m, y_n)$, is written $(x_{mn}, y_{mn})$. The relationship between the positions of the centroids of the spots in the spot distribution received by the CCD 26 of the sensor system 22 and the refractive state of the eye being measured may be expressed by equation 8.

$$\begin{cases} x_{mn} = [1 - (M + J_0) \cdot f] \cdot x_m - J_{45} \cdot f \cdot y_n \\ y_{mn} = -J_{45} \cdot f \cdot x_m + [1 - (M - J_0) \cdot f] \cdot y_n. \end{cases} \qquad \text{equation 8}$$

Equation 8, or approximations, equivalents or alternatives to equation 8 that will be apparent to those in the art, may serve as a basis for determining the refractive state of a subject eye from the spot distribution received by the CCD 26. Example methods of determining the refractive state of the subject eye are mathematically described in the following sections. The sections include a description of a derivation of the mathematical description for the purposes of explanation of the background to the methods. As previously described, the mathematical description is readily implemented by a suitable computational device, for example a microprocessor device or digital signal processing device, in hardware such as an ASIC, or in firmware, such as a programmable logic device.

6.1. Computational Methods A1 and A2: Linear regression analysis of selected meridians In Method A1, the first step is to find the positions of the centroids and to record them in a data file or (N×N) array. Various methods of finding the position of the centroids may be used, including for example using a center of mass calculation in a region of interest of the CCD array corresponding to a given lenslet, finding the intensity peak in a region of interest, or a combination of intensity thresholding and windowing, and center of mass calculations.

The sphere and cylinder are then extracted by performing a linear regression of the centroid positions along different directions. For instance, the refractive state can be calculated by finding the positions of the spots along the central column $(x_{0n}, y_{0n})$ and the central row $(x_{m0}, y_{m0})$ of the array. According to equation 8, the corresponding spot positions are shown in the relations in equation 9a.

$$\begin{cases} x_{0n} = -J_{45} \cdot f \cdot y_n \\ y_{0n} = [1 - (M - J_0) \cdot f] \cdot y_n \\ x_{m0} = [1 - (M + J_0) \cdot f] \cdot x_m \\ y_{m0} = -J_{45} \cdot f \cdot x_m \end{cases} \quad \text{equation 9a}$$

A linear regression of experimental data will provide values for the 4 slopes, as shown in equation 9b.

$$\begin{cases} sx_{0n} = -J_{45} \cdot f \\ sy_{0n} = 1 - (M - J_0) \cdot f \\ sx_{m0} = 1 - (M + J_0) \cdot f \\ sy_{m0} = -J_{45} \cdot f \end{cases} \quad \text{equation 9b}$$

The equations collectively shown in equation 9b form a system of 4 equations with 4 unknowns, which can be solved in a computational system to find the values of f, M, $J_0$ and $J_{45}$. Alternatively, the computational system can be calibrated to provide a value for f. In that case, only three of the equations are needed to extract the refractive state.

An example calibration process comprises:
Mounting the wavefront sensor on a translation stage or rail on an optical bench;
Aligning the wavefront sensor with the beam emitted by an infrared superluminescent diode coupled to a single-mode fiber. The single mode fiber produces a spherical wavefront. The radius of this spherical wavefront is equal to the distance from the fiber to the lenslet array;
Recording the spot pattern produced for many different positions of the fiber;
Calculating the spot separation as a function of fiber to lenslet distance; and
From the spot separation, calculating the focal length of the lenslet using equation 9b.

In Method A2, the linear regression is performed along the two diagonals of the array of centroids. Using equation 7 the positions of the centroids corresponding to lenslets centered at positions $x_m = y_n$ are given by equation 10.

$$\begin{cases} x_{mn}^+ = [1 - (M + J_0 - J_{45}) \cdot f] \cdot x_m \\ y_{mn}^+ = [1 - (M - J_0 + J_{45}) \cdot f] \cdot x_m \end{cases} \quad \text{equation 10}$$

Similarly, equation 11 shows the relation for the centroids corresponding to lenslets centered at position $x_m = -y_n$.

$$\begin{cases} x_{mn}^- = [1 - (M + J_0 + J_{45}) \cdot f] \cdot x_m \\ y_{mn}^- = [-1 + (M - J_0 - J_{45}) \cdot f] \cdot x_m \end{cases} \quad \text{equation 11}$$

As with Method A1, calculating the four slopes of linear regressions of experimental data using the four above equations will provide the values of sphere and cylinder. Alternatively, the regressions can be performed on the relations shown in equation 12, or any other, linear combination of the above four equations:

$$\begin{cases} x_{mn}^+ + y_{mn}^+ = 2 \cdot (1 - M) \cdot f \cdot x_m \\ x_{mn}^+ - y_{mn}^+ = 2 \cdot (J_{45} - J_0) \cdot f \cdot x_m \\ x_{mn}^- + y_{mn}^- = -2 \cdot J_0 \cdot f \cdot x_m \\ x_{mn}^- - y_{mn}^- = 2 \cdot [1 + (J_{45} - M)] \cdot f \cdot x_m \end{cases} \quad \text{equation 12}$$

6.2. Computational Method B: Least square analysis

In Method B, the centroid positions $(x_{mn}^*, y_{mn}^*)$ recorded during a measurement are compared to the positions $(x_{mn}, y_{mn})$ predicted by the theoretical equation 7 using a least square error method. To simplify the notation, equation 7 is re-written as equation 13a.

$$\begin{pmatrix} y_{mn} \\ y_{mn} \end{pmatrix} = \begin{pmatrix} A & B \\ B & D \end{pmatrix} \cdot \begin{pmatrix} x_m \\ y_n \end{pmatrix}. \quad \text{equation 13a}$$

The coefficients A, B and D in equation 13a are defined in equation 13b.

$$\begin{cases} A = 1 - (M + J_0) \cdot f \\ B = -J_{45} \cdot f \\ D = 1 - (M - J_0) \cdot f \end{cases} \quad \text{equation 13b}$$

In some embodiments, the coefficients A, B and D are found by minimizing the two error functions in equation 14.

$$\begin{cases} E_x = \sum_m \sum_n [x_{mn}^* - (A \cdot x_m + B \cdot y_n)]^2 \\ E_y = \sum_m \sum_n [y_{mn}^* - (B \cdot x_m + D \cdot y_n)]^2 \end{cases} \quad \text{equation 14}$$

For instance, the error function $E_x$ is minimized when:

$$\frac{\partial E_x}{\partial A} = \frac{\partial E_x}{\partial B} = 0$$

Which can be expressed as:

$$\sum_m \sum_n x_m \cdot (x_{mn}^* - A \cdot x_m - B \cdot y_n) = 0$$

$$\sum_m \sum_n y_n \cdot (x_{mn}^* - A \cdot x_m - B \cdot y_n) = 0$$

Which leads to the system of two equations shown in equation 15, which can be solved in a suitably programmed or designed computational system to find the values of A and B.

$$\begin{cases} A \cdot N \cdot \sum_m x_m^2 + B \cdot \sum_m \left(x_m \cdot \sum_n y_n\right) = -\sum_m \left(x_m \cdot \sum_n x_{mn}^*\right) \\ A \cdot \sum_m \left(x_m \cdot \sum_n y_n\right) + B \cdot N \cdot \sum_n y_n^2 = -\sum_n \left(y_n \cdot \sum_m x_{mn}^*\right) \end{cases} \quad \text{equation 15}$$

where N is the dimension of the N×N lenslet array. A similar derivation for the error function $E_y$ produces the system of equations shown in equation 16, which can be solved to find B and D.

$$\begin{cases} B \cdot N \cdot \sum_m x_m^2 + D \cdot \sum_m \left(x_m \cdot \sum_n y_n\right) = -\sum_m \left(x_m \cdot \sum_n y_{mn}^*\right) \\ B \cdot \sum_m \left(x_m \cdot \sum_n y_n\right) + D \cdot N \cdot \sum_n y_n^2 = -\sum_n \left(y_n \cdot \sum_m x_{mn}^*\right) \end{cases} \quad \text{equation 16}$$

The refractive state can be calculated from the three coefficients A, B, D, by using equation 13b.

In alternative embodiments to that using Method B, other typical statistical methods, including iterative algorithms or optimization techniques, can be used to find the coefficients A, B and D of equation 13a, which minimize the error between the experimental dataset and the set of values predicted from the theoretical equation 7.

Examples of iterative or optimization techniques that can be employed for this purpose include a simplex algorithm, a gradient-descent algorithm, or a non-linear least-square technique such as the Levenberg-Marquard algorithm.

6.3. Computational Method C: Calculation of the refractive state by Fourier analysis In overview, in Method C, the analysis of the Hartmann-Shack spots is performed in the frequency domain. Unlike Methods A and B, this technique does not require calculation of the spot centroids. In addition, the main assumption is that the intensity distribution is the same in each spot.

Fourier Transform Description of the Hartmann-Shack Image

In the following description, where a variable is referred to that was used in the description of Methods A and B, that variable has been described using the same notation. For example N refers to the N×N array of lenslets.

If incoherent superposition is assumed, the intensity distribution recorded by the image sensor, e.g. CCD 26, can be described by equation 17.

$$I(x, y) = \sum_m \sum_n h_{mn}(x, y). \quad \text{equation 17}$$

In equation 17, $h_{mn}(x,y)$ is the intensity distribution of the spot corresponding the lenslet centered at $(x_m, y_n)$ and:

$$-\frac{N-1}{2} \leq m, n \leq \frac{N-1}{2}$$

The intensity distribution $h_{mn}(x,y)$ is the diffraction pattern produced by the lenslet. The exact diffraction pattern of each spot is determined by the aperture function and focal length of the lenslet and the wavefront error. In approximation, to simplify the calculations, it is assumed that each lenslet produces the same diffraction pattern, h(x,y). In that case, the intensity distribution $h_{mn}(x,y)$ can be written as equation 18.

$$h_{mn}(x,y) = h(x - x_{mn}, y - y_{mn}) \quad \text{equation 18}$$

Substituting into equation 18 from equation 13 results in equation 19.

$$h_{mn}(x,y) = h(x - A \cdot x_m - B \cdot y_n, y - B \cdot x_m - D \cdot y_n) \quad \text{equation 19}$$

Equation 19 yields the expression in equation 20 for the intensity distribution recorded by the image sensor.

$$I(x, y) = \sum_m \sum_n h(x - A \cdot x_m - B \cdot y_n, y - B \cdot x_m - D \cdot y_n). \quad \text{equation 20}$$

The Fourier transform of the intensity distribution, I(u, v) is shown in equation 21.

$$I(u, v) = \sum_m \sum_n H(u, v) \cdot e^{-2\pi j \cdot [(A \cdot x_m + B \cdot y_n)u + (B \cdot x_m + D \cdot y_n)v]}. \quad \text{equation 21}$$

In equation 21, u and v are the spatial frequencies and H(u,v) is the Fourier transform of h(x,y). This equation can be re-written as equation 22 or equation 23.

$$I(u, v) = H(u, v) \cdot \sum_m \sum_n e^{-2\pi j [(A \cdot u + B \cdot v) \cdot x_m + (B \cdot u + D \cdot v) \cdot y_n]}. \quad \text{equation 22}$$

$$I(u, v) = \quad \text{equation 23}$$

$$H(u, v) \cdot \sum_{m=-\frac{N-1}{2}}^{\frac{N-1}{2}} e^{-2\pi j \cdot p \cdot (A \cdot u + B \cdot v) \cdot m} \cdot \sum_{n=-\frac{N-1}{2}}^{\frac{N-1}{2}} e^{-2\pi j \cdot p \cdot (B \cdot u + D \cdot v) \cdot n}.$$

Each sum is a Dirichlet kernel, of the form shown in equation 24.

$$\sum_{n=-N}^{N} e^{j \cdot n \cdot x} = \frac{\sin\left(\frac{(2N+1) \cdot x}{2}\right)}{\sin\left(\frac{x}{2}\right)}. \quad \text{equation 24}$$

Combining equations 23 and 24 yields the expression in equation 25 for the Fourier transform of the Hartmann-Shack spot pattern, where the coefficients A, B and D are related to the refractive error as defined in equation 13b.

$$I(u, v) = H(u, v) \cdot \frac{\sin[N \cdot \pi \cdot p \cdot (A \cdot u + B \cdot v)]}{\sin[\pi \cdot p \cdot (A \cdot u + B \cdot v)]} \cdot \quad \text{equation 25}$$

$$\frac{\sin[N \cdot \pi \cdot p \cdot (B \cdot u + D \cdot v)]}{\sin[\pi \cdot p \cdot (B \cdot u + D \cdot v)]}$$

Equation 25 shows that the Fourier transform is the product of the Fourier transform of the diffraction pattern of each spot, multiplied by two Dirichlet kernels. When N tends to infinity, the Dirichlet kernels become a set of peaks (Dirac distributions) of amplitude N located at positions shown in equation 26.

$$\begin{cases} A \cdot u + B \cdot v = \dfrac{i}{p} \\ B \cdot u + D \cdot v = \dfrac{j}{p} \end{cases}.$$ equation 26

Where i and j are integers (positive or negative). Each of the two equations in equation 26 corresponds to a set of parallel lines. The first set of lines are parallel lines with a slope of −A/B. These lines are parallel to the vector in equation 27.

$$r = \begin{pmatrix} B \\ -A \end{pmatrix} = \begin{pmatrix} -J_{45} \cdot f \\ -1 \to (M + J_0) \cdot f \end{pmatrix}.$$ equation 27

The second set of lines are parallel lines with a slope of −B/D. These lines are parallel to the vector in equation 28.

$$s = \begin{pmatrix} D \\ -B \end{pmatrix} = \begin{pmatrix} 1 - (M - J_0) \cdot f \\ J_{45} \cdot f \end{pmatrix}.$$ equation 28

The intersection of these sets of lines gives the position of the primary intensity peaks of the Fourier transform of the spot distribution. In other words, for large values of N, the Fourier transform is itself a distribution of discrete spots with centroids located at the intersection of the two sets of lines defined by the above equation. For small values of N, there will be a set of secondary peaks.

The primary intensity peaks are located at the frequencies defined in equation 29 or equation 30.

$$\begin{cases} u_{ij} = \dfrac{1}{p} \cdot \dfrac{D \cdot i - B \cdot j}{A \cdot D - B^2} \\ v_{ij} = -\dfrac{1}{p} \cdot \dfrac{B \cdot i - A \cdot j}{A \cdot D - B^2} \end{cases}.$$ equation 29

$$\begin{cases} u_{ij} = \dfrac{1}{p} \cdot \dfrac{[1 - (M - J_0) \cdot f] \cdot i + J_{45} \cdot f \cdot j}{[1 - (M + J_0) \cdot f] \cdot [1 - (M - J_0) \cdot f] - J_{45}^2 \cdot f^2} \\ v_{ij} = -\dfrac{1}{p} \cdot \dfrac{-J_{45} \cdot f \cdot i - [1 - (M + J_0) \cdot f] \cdot j}{[1 - (M + J_0) \cdot f] \cdot [1 - (M - J_0) \cdot f] - J_{45}^2 \cdot f^2} \end{cases}.$$ equation 30

In the absence of refractive error, A=D=1 and B=0. In that case the Fourier transform is defined by equation 31.

$$I(u,v) = H(u,v) \cdot \dfrac{\sin[N \cdot \pi \cdot p \cdot u]}{\sin[\pi \cdot p \cdot u]} \cdot \dfrac{\sin[N \cdot \pi \cdot p \cdot v]}{\sin[\pi \cdot p \cdot v]}.$$ equation 31

The Fourier transform defined in equation 31 is a set of spots arranged in a regular grid pattern centered around the zero frequency. The spots are centered at frequencies shown in equation 32.

$$\begin{cases} u_{ij} = \dfrac{i}{p} \\ v_{ij} = \dfrac{j}{p} \end{cases}.$$ equation 32

In the presence of a spherical refractive error, the Fourier transform is defined by equation 33.

$$I(u,v) = H(u,v) \cdot \dfrac{\sin[N \cdot \pi \cdot p \cdot (1 - M \cdot f) \cdot u]}{\sin[\pi \cdot p \cdot (1 - M \cdot f) \cdot u]} \cdot$$ equation 33
$$\dfrac{\sin[N \cdot \pi \cdot p \cdot (1 - M \cdot f) \cdot v]}{\sin[\pi \cdot p \cdot (1 - M \cdot f) \cdot v]}.$$

The Fourier transform is a set of spots arranged in a grid pattern centered around the zero frequency. The spots are centered at frequencies shown in equation 34.

$$\begin{cases} u_{ij} = \dfrac{i}{p \cdot (1 - M \cdot f)} \\ v_{ij} = \dfrac{j}{p \cdot (1 - M \cdot f)} \end{cases}.$$ equation 34

Similarly, in the presence of cylinder with axis a=0 ($J_{45}$=0), the Fourier transform is a set of spots arranged in a grid pattern centered around the zero frequency. The spots are centered at frequencies shown in equation 35.

$$\begin{cases} u_{ij} = \dfrac{i}{p \cdot [1 - (M + J_0) \cdot f]} \\ v_{ij} = \dfrac{j}{p \cdot [1 - (M - J_0) \cdot f]} \end{cases}.$$ equation 35

The addition of a cross-cylinder term $J_{45}$ produces a rotation of the spot pattern around the center frequency by an amount that is directly related to the value of the $J_{45}$ cross-cylinder.

The preceding description shows that both sphere and cylinder can be extracted from a frequency domain analysis of the spot patterns. The utilisation of the mathematical properties described above in a computational system receiving as an input a measurement from a Hartmann-Shack sensor system is described below.

6.3.1. Methods C1 and C2 : Extraction of the sphere and cylinder from the Fourier transform In Method C1, the values of A, B and D are found from the frequency of centroids forming the top right quadrant surrounding the center frequency (u=0, v=0). The relations in equation 36 are derivable from equation 29.

$$\begin{cases} u_{01} = -\dfrac{B}{p} \cdot \dfrac{1}{A \cdot D - B^2} \\ v_{01} = \dfrac{A}{p} \cdot \dfrac{1}{A \cdot D - B^2} \end{cases}$$ equation 36
$$\begin{cases} u_{10} = \dfrac{D}{p} \cdot \dfrac{1}{A \cdot D - B^2} \\ v_{10} = -\dfrac{B}{p} \cdot \dfrac{1}{A \cdot D - B^2} \end{cases}.$$
$$\begin{cases} u_{11} = \dfrac{1}{p} \cdot \dfrac{D - B}{A \cdot D - B^2} \\ v_{11} = -\dfrac{1}{p} \cdot \dfrac{B - A}{A \cdot D - B^2} \end{cases}$$

The first two sets of equation in equation 36 give a relation between A and B, and D and B as shown in equation 37, which in turn indicates the relations in equation 38.

$$\frac{u_{01}}{v_{01}} = -\frac{B}{A}$$

$$\frac{u_{10}}{v_{10}} = -\frac{D}{B}.$$

equation 37

$$A = -B \cdot \frac{v_{01}}{u_{01}}$$

$$D = -B \cdot \frac{u_{10}}{v_{10}}.$$

equation 38

Combining the relations in equation 38 with the expression of $u_{11}$ gives equation 39.

$$B = -\frac{1}{p} \cdot \frac{u_{01}}{u_{11}} \cdot \frac{u_{10} + v_{10}}{v_{01} \cdot u_{10} - u_{01} \cdot v_{10}}$$

$$A = -\frac{1}{p} \cdot \frac{v_{01}}{u_{11}} \cdot \frac{u_{10} + v_{10}}{v_{01} \cdot u_{10} - u_{01} \cdot v_{10}}$$

$$D = -\frac{1}{p} \cdot \frac{u_{01}}{u_{11}} \cdot \frac{u_{10}}{v_{10}} \cdot \frac{u_{10} + v_{10}}{u_{10} - u_{01} \cdot v_{10}}.$$

equation 39

From equation 39, values for $J_{45}$, $J_0$ and M are defined as shown in equation 40.

$$J_{45} = -\frac{1}{p \cdot f} \cdot \frac{u_{01}}{u_{11}} \cdot \frac{u_{10} + v_{10}}{v_{01} \cdot u_{10} - u_{01} \cdot v_{10}}$$

$$J_0 = \frac{1}{2 \cdot f \cdot p} \cdot \frac{1}{u_{11}} \cdot \frac{u_{10} + v_{10}}{v_{01} \cdot u_{10} - u_{01} \cdot v_{10}} \left( v_{01} - u_{01} \cdot \frac{u_{10}}{v_{10}} \right)$$

$$M = \frac{1}{f} + \frac{1}{2pf} \cdot \frac{1}{u_{11}} \cdot \frac{u_{10} + v_{10}}{v_{01} \cdot u_{10} - u_{01} \cdot v_{10}} \cdot \left( v_{01} + u_{01} \cdot \frac{u_{10}}{v_{10}} \right).$$

equation 40

In some embodiments, to improve the reliability of the measurement, similar calculations are repeated on the remaining three quadrants surrounding the central frequency. These similar calculations are in essence redundant, but may be combined by averaging, selecting the median or otherwise. Of course, in other embodiments, one or more of the other quadrants may be used instead of the upper right quadrant described above.

In method C2, a least square method similar to method B1, an iterative method, or an optimization technique, is used to find the rotation angle and scaling factor between the regular grid pattern produced when a planar wave is incident on the lenslet and the distorted grid pattern produced by the presence of sphere and cylinder.

7. Example 2—Operation Microscope Mounted Refractor

In other embodiments, the refractor is an "inside-coupled" design. In this type of design the refractor is integrated with the surgical microscope.

Figure 10:
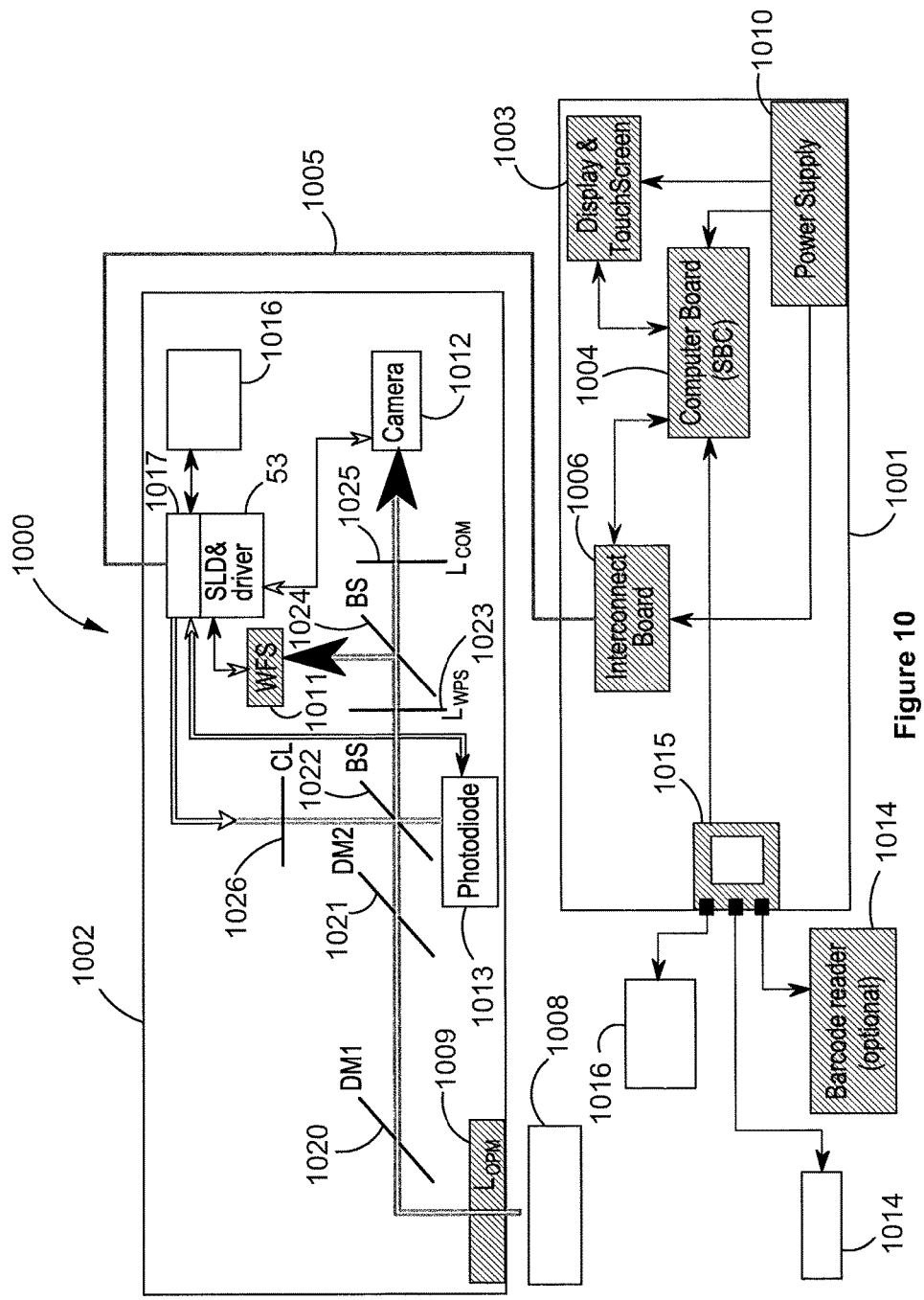
FIG. 10: shows a diagrammatic representation of an embodiment of an ophthalmic refractor.

FIG. 10 shows an embodiment of an inside-coupled intraoperative autorefractor (IAR) 1000. The IAR 1000 consists of two modules, a console 1001 and an optical module 1002. The console 1001 has a user interface that includes a display and touch screen 1003, and a computer, in this embodiment a single board computer 1004 that acquires data from the optical module 1002, performs data processing, controls the user interface, and controls components in the optical module 1002. The optical module 1002 is configured or is configurable to measure the refractive error of the patient's eye in real-time during a surgical procedure. The results of the measurement are displayed on the display and touch screen 1003 of the console 1001.

The console 1001 and optical module 1002 are in communication for example via an electrical cable 1005 connecting a console interface 1006 (e.g. an interconnect board) and an optical module interface 1017 (e.g. an interconnect board). The optical module interface 1017 is connected to a superluminescent light-emitting diode (SLD) and its driver 53. The interface 1017 and SLD circuitry 53 may of course be implemented on the same or separate physical hardware boards and connected in an appropriate way as would be clear to a person skilled in the art.

The console 1001 is a stand-alone component that can be mounted, for example on a cart, pole, desk, etc. The optical module 1002 mechanically attaches to an operation microscope (OPMI) 1008 so that the optical axes of the OPMI 1008 and of the optical module 1002 of the JAR 1000 coincide, without obstructing the view from the OPMI 1008. The optical module 1002 mounts to the OPMI 1008 by using a dove-tail adaptor which matches the dove-tail mount of the microscope 1008. In the embodiment shown, the OPMI 1008 and optical module 1002 share an objective lens 1009. Prior to mounting the optical module 1002, the original objective lens (not shown) of the OPMI is removed and replaced by the shared objective lens 1009 which is centered on the optical axis of the microscope 1008 when the optical module 1002 is mounted. When the optical module 1002 is installed, the operator is able to use the OPMI 1008 normally.

7.1. Description of the Console

The console 1001 contains a single board computer (SBC) 1004, touch-screen monitor 1003, and power supply 1010. The SBC 1004 runs a graphical user interface (GUI) and interfaces with the data acquisition devices of the optical module 1002 (including the wavefront sensor (WFS) 1011, camera 1012 and photodiode 1013). A hardware interface 1015 allows interfacing with the optical module 1002, as well as with one or more memory devices 1016 and other hardware, such as a barcode reader 1014 which may be included, for example to input or verify patient data.

The power supply 1010 provides low voltage DC power to all of the system components. The console 1001 is connected to the other components of the system through, for example, cables and connectors via the interfaces 1006 and 1017.

Figure 11:
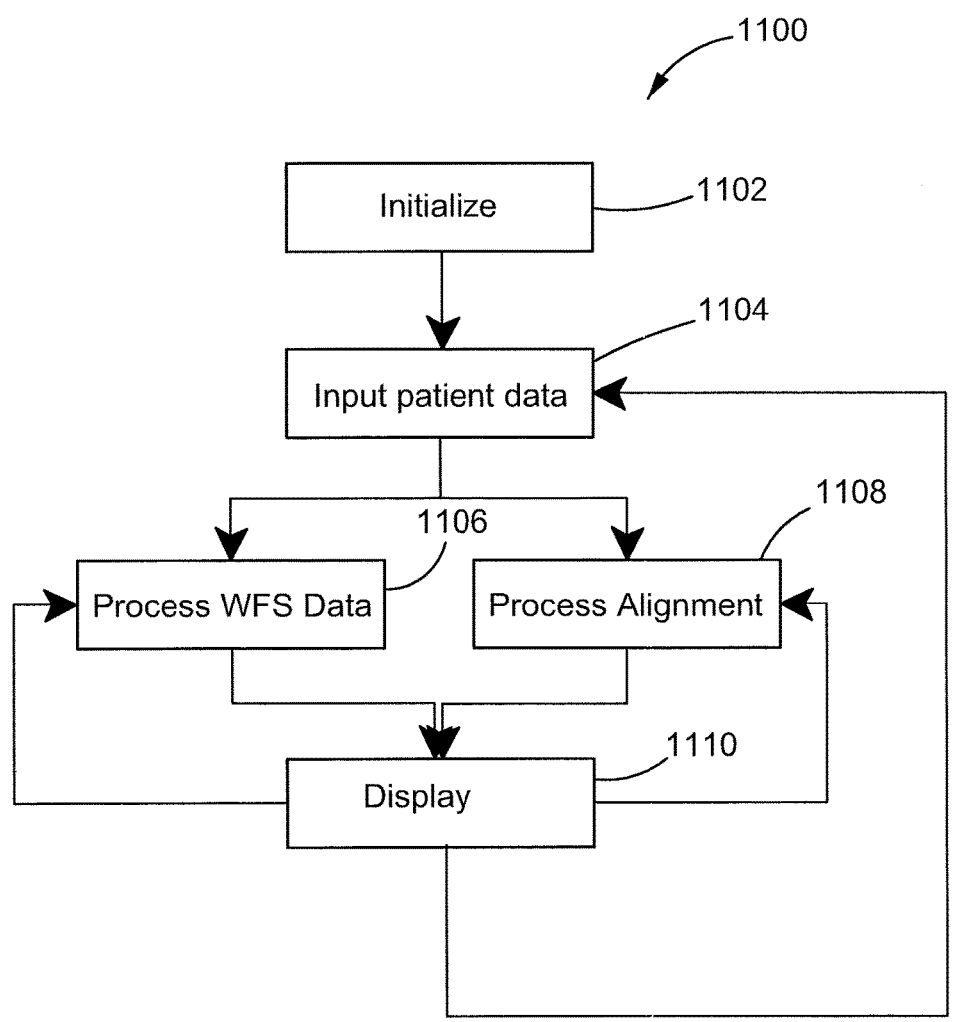
FIG. 11: shows a flow diagram of the process by which the refractor of FIG. 10 takes and displays measurements.

The SBC 1004 of the console 1001 includes instructions that, when executed, are used to control the IAR 1000 for inputting, processing and outputting data. The software runs on a multi-core CPU (not shown) that forms part of the SBC 1004. FIG. 11 shows a flow diagram 1100 of an algorithm that, when executed, may be used to control the IAR 1000 for inputting, processing and outputting data.

Step 1102 is an initialization step. Upon startup the software initializes the hardware components (WFS 1011, SLD 53, camera 1012) and checks for proper functioning of these devices. It reads configuration and calibration data specific to the optical module from a memory device 1016 (e.g. a USB memory device, or other suitable memory device) via a hardware interface 1015. This data allows the software to process WFS data and Camera data accurately. During the initialization step 1102, processing intensive tasks are allocated to different cores in the CPU.

Patient data is input at step 1104. After initialization 1102 the software progresses to patient related inputs. Data such as (but not limited to) patient identification and notes can be entered and the system is trained for the patient's pupil using the camera 1012. User data is entered via a user interface, for example an on-screen keyboard using the device's touch screen.

At step 1106 WFS data is processed. The software in a continuous loop reads data from the WFS 1011 and processes the data. It reads raw data from the WFS 1011 approximately 5-6 times per second and averages this data. (Data may be read more, or less, often depending on the user requirements and/or technology e.g. available memory or sensor speed). The data is used to calculate the patient's refractive error (where the refractive error may be defined in terms of the spherical power, cylindrical power and/or axis angle etc.) using the calibration data read during initialization 1102. The spherical power, cylindrical power and axis angle values are stored internally in a circular buffer and are available for the display process (at step 1110 described below) at any time. The WFS data processing 1106 is allocated to one core of the multi-core CPU and in some embodiments may be the only process running on this core.

Alignment is Processed at Step 1108. In a continuous loop the software assesses the alignment of the patient pupil with the device using data read from the alignment camera and supplemented by data from the WFS 1011. The process stores the alignment results in a circular buffer for the display process 1110. Alignment is assessed by performing a pattern recognition of the alignment camera image using initial estimates obtained during the input of patent data 1104 in the software process. Alignment is assessed at least twice per second. In some embodiments, processing alignment 1108 is allocated to one core of the multi-core CPU and may be the only process running on this core. In some embodiments the core used for processing alignment 1108 may be a different core to the one used for processing WFS data 1106.

The Display Process is Performed at Step 1110. The display process 1110 updates the display once per second with refractive data. This may be done less or more often depending on, for example, user requirements or the performance of the technology used. The display process 1110 asynchronously reads data from the circular buffer maintained by the WFS data processing step 1106 for the data to display. The display process 1110 also reads the alignment results from the alignment processing step 1108 and updates a symbol on the alignment camera video screen showing the relative location of the measurement area and patient pupil. The display process 1110 also displays a warning if the pupil and measurement area are misaligned by more than a given threshold. The threshold is read during initialization 1102 from the configuration data. The display process 1110 can display the data (spherical power, cylindrical power and/or axis angle etc.) either numerically or graphically. In the graphical plot, a preceding period of time (for example the previous 10 seconds of data) is displayed in a scrolling chart. The display process 1110 is responsible for the overall graphical user interface and in one embodiment is allocated to a third core of the multi-core CPU.

At any given time a user may end the display process and return to the input patent data step 1104 to prepare the device for a new patient. Prior to re-entering step 1104, the user can save measured data (for example to a USB device attached to the console, or other appropriate memory device).

7.2. Description of the Optical Module

Referring again to FIG. 10, the optical module 1002 contains a near-infrared (NIR) superluminescent light-emitting diode (SLD) 53. The output from the SLD 53 is collimated and directed to the center of the patient's pupil, generally parallel to the line of sight of the eye. The NIR beam is diffusely reflected by the retina. The diffuse reflected wave passes through the patient's eye, back into the IAR 1000 where the wavefront properties (spherical power, cylindrical power and/or axis angle etc.) are measured using the WFS 1011.

Above the objective lens 1009, the optical module 1002 contains a dichroic mirror (DM1 in FIG. 10), which transmits visible wavelengths towards the OPMI 1008 and reflects NIR near-infrared wavelengths towards the wavefront sensor WFS 1011 and an infrared camera 1012 via a camera lens 1025. The dichroic mirror 1020 DM1 also transmits visible light emitted by the OPMI illumination system to the eye.

The optical module 1002 contains a glass plate (not shown) as a place holder for additional diagnostic or imaging devices, such as an optical coherence tomography system (OCT) that allows simultaneous imaging and measurement of refraction. The glass plate is replaced for instance by a second dichroic mirror 1021 (as shown by DM2 in FIG. 10) for embodiments including the additional hardware.

The optical module 1002 also includes a photodiode 1013 that measures a small fraction of the emission of the SLD 53 transmitted via a collimator 1026 and polarizer (not shown in FIG. 10) through a beam splitter 1022 (BS in FIG. 10). The purpose of the photodiode 1013 is to continuously monitor the state of the SLD 53. In the event of a fault condition, the photodiode 1013 allows the system to determine if the fault condition is due to a failure of the SLD 53.

The objective lens 1009 ($L_{OPMI}$ in FIG. 10) and the WFS lens 1023 ($L_{WFS}$ in FIG. 10) image the wavefront at the reference plane 1201 (see FIG. 12) onto the lenslet array of the wavefront sensor (WFS) 1011. The reference plane 1201 is located approximately 25 to 50 mm above the focal point of the objective lens 1009. The WFS 1011 is connected to the computer 1004 inside the console 1001, e.g. via a cable 1005 and via the hardware interface 1015.

The camera 1012 uses the lens 1025 to create a NIR image of the front of the eye. The image helps the operator to align the IAR 1000 with the patient's eye. This camera 1012 is connected to the console 1001, e.g. with a cable 1005 and via the hardware interface 1015.

Figure 12:
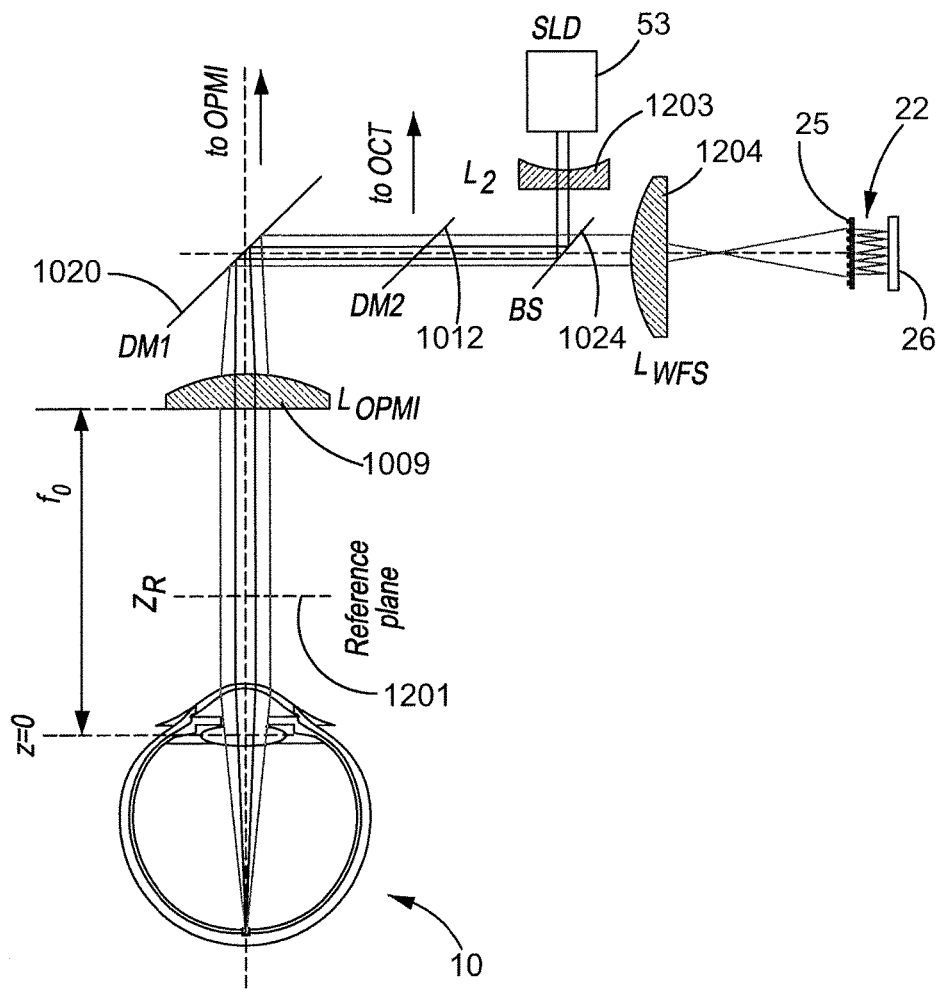
FIG. 12: shows a diagrammatic representation of optical components of the refractor of FIG. 10.

FIG. 12 shows a diagrammatic representation 1200 of the optical module of the refractor of FIG. 10. In the inside-coupled design, the objective lens $L_{OPMI}$ 1009 of the surgical microscope (OPMI) 1008 is used to deliver the light beam. Since the refracted beam would also pass through the objective lens of the microscope, the working space for the surgeon is determined by the objective focal length and is not reduced by the thickness of the device.

The inside-coupled intraoperative autorefractor (IAR) 1000 is coupled to the rest of the microscope OPMI (not shown) via a dichroic beam splitter DM1 1020. In the embodiment shown the beam splitter DM1 1020 provides light for both the optical module 1002 of the autorefractor and an optical coherence tomograph system (OCT) (not shown). The OCT is not an essential part of the inside-coupled design and is included to illustrate the principle that other measurements may be taken simultaneously with refraction. Dichroic mirror DM2 1021 transmits the OCT beam and reflects the refractor beam (or vice versa) and is used to combine the OCT and refractor beams. The beam splitter BS 1024 performs functions comparable to the beam splitter 906 (see FIG. 9).

A probe beam is generated by the diode 53, which as explained may be a superluminescent diode SLD, and is delivered by the beam splitter BS 1024 and dichroic mirrors DM2 1021 and DM1 1020, through the microscope objective lens 1009. In some embodiments a lens $L_2$ 1203 between a collimator (not shown in FIG. 12) and the lens 1009 is included to produce a beam expander. This ensures that the probe beam remains collimated when it is transmitted through the lens 1009. In other embodiments the Lens $L_2$ 1203 is omitted, which may allow for a more compact system.

In use, the surgeon or other operator positions the lens 1009 relative to the subject eye 10 so that the focal distance $f_0$ of the lens 1009 coincides with the pupil plane. The reference plane $Z_R$ 1201 is imaged onto the lenslet array 25 using an air-spaced imaging doublet: the first lens of the doublet is the microscope objective 1009; the second lens is a wavefront sensor lens 1204. In some embodiments the wavefront sensor lens 1204 is selected so that the reference plane is imaged with a magnification of m=−1 on the lenslet array 25. As explained herein, magnification factors other than unity may also be used.

It can be shown that the measurement error of the refractor is related to the distance separating the two lenses of the doublet, 1009 and 1204. Accordingly, in certain embodiments this distance is minimized to 150 mm or less, more preferably 100 mm or less and even more preferably 50 mm or less.

7.3. Implementation of the Optical Module

Figure 13A:
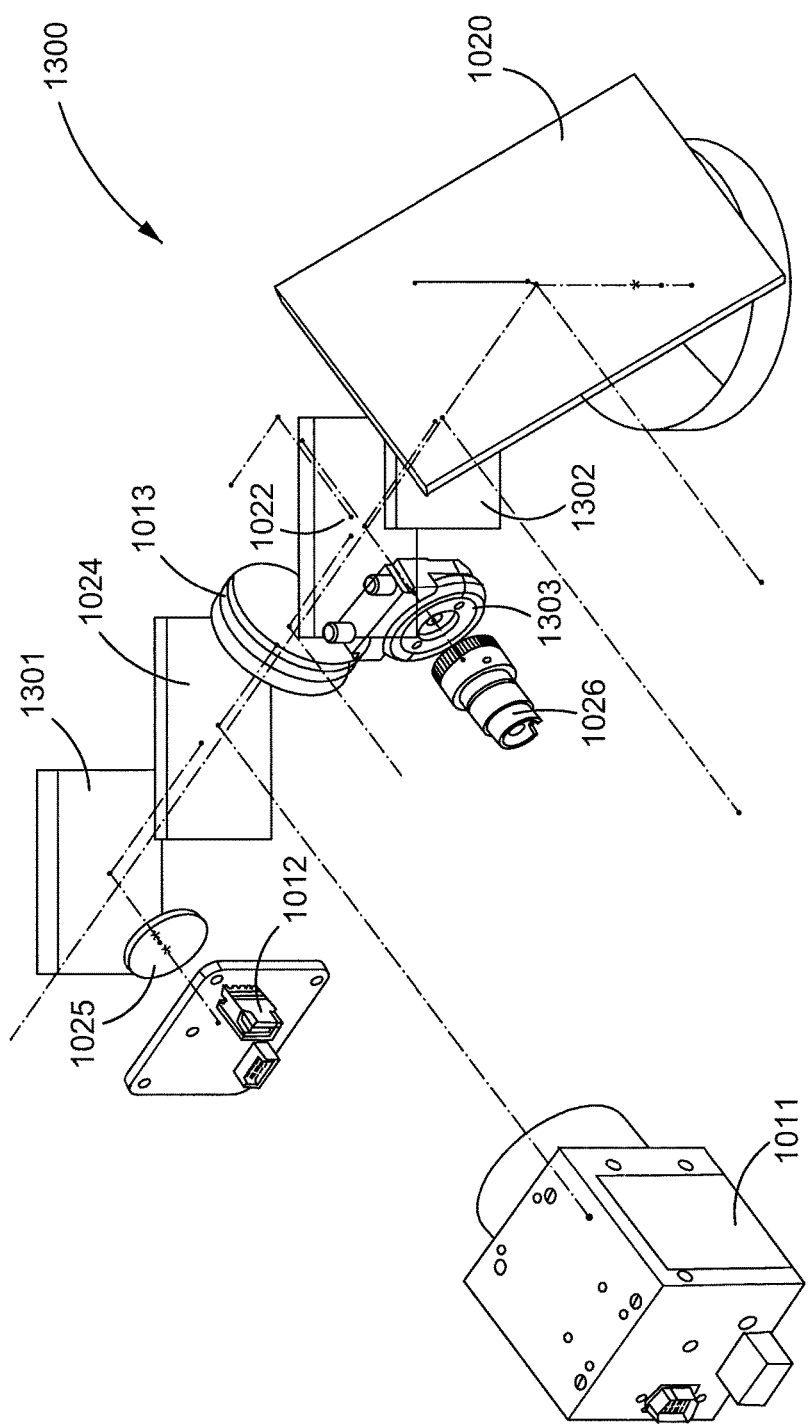
FIG. 13A: shows a schematic diagram of a perspective view of the mechanical layout of the optical module shown in FIG. 10.
Figure 13B:
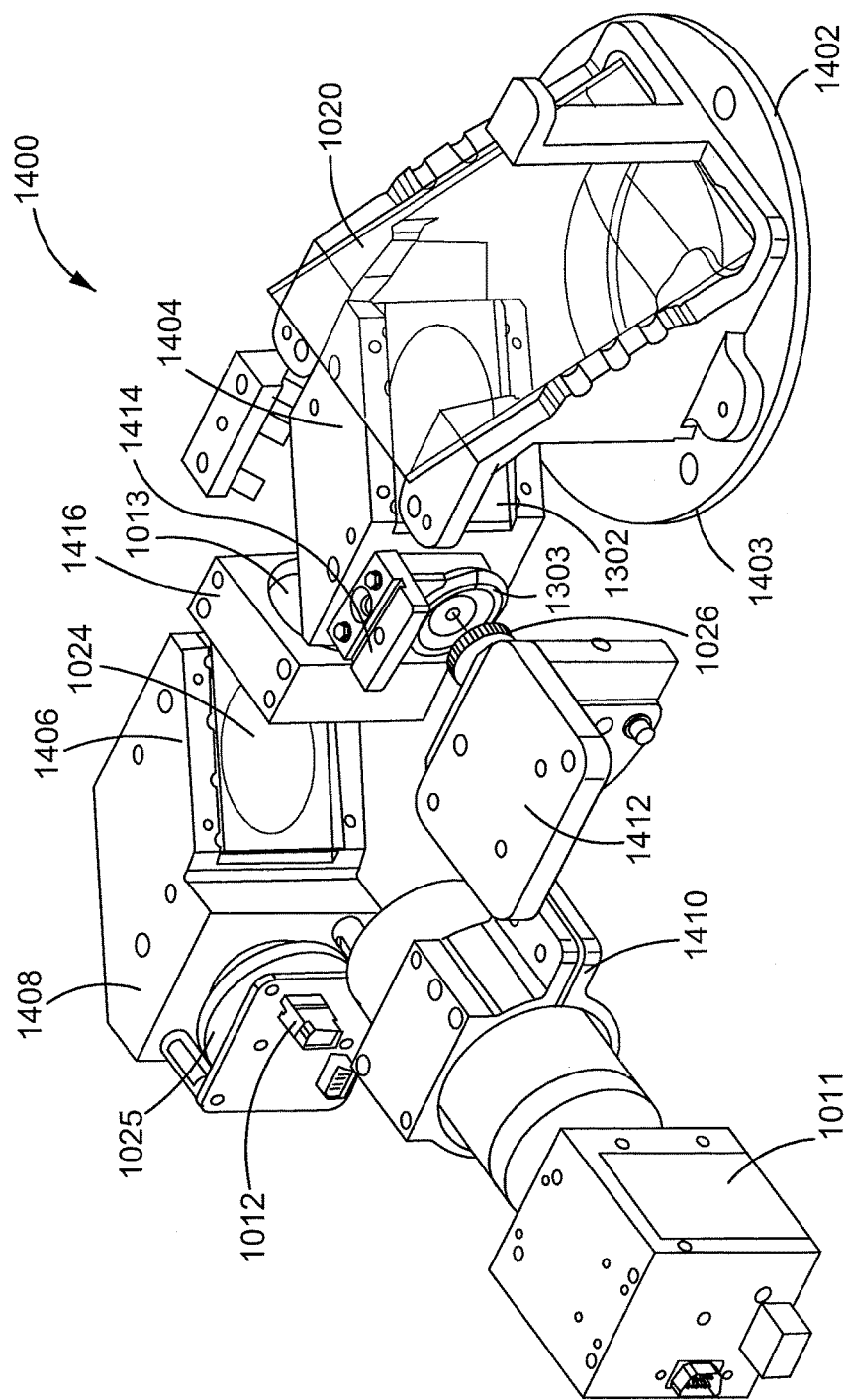
FIG. 13B: shows a perspective view of the mounted components illustrated in FIG. 13A.

FIG. 13A shows a schematic diagram 1300 of a perspective view of the mechanical layout of the optical module 1002 shown in FIG. 10, and FIG. 13B shows a perspective view of the mounted components illustrated in FIG. 13A.

The optical layout of the IAR 1000 is arranged in 3-D space in such a way as to minimize the height and volume of the device. Reference numerals in FIGS. 13 and 14 that are the same as those used in FIG. 10 refer to the same components. In particular, FIG. 13A shows the components in of the optical path from the OPMI 1008 (not shown in FIG. 13A) to the camera 1012 from the dichroic mirror DM1 1020, through the glass plate 1302 (replaced by DM2 1021 in FIG. 10), a photodiode (not shown), beam splitter 1024, folding mirror 1301, camera lens 1025 and finally camera 1012. Also shown are the collimator 1026 and a polarizer 1303, as well as the WFS 1011.

Referring to the mounted components 1400 shown in FIG. 13B, the following mount parts are used for the IAR 1000:

Objective Mount 1402
DM1 Mount 1403
BS1 Mount 1404
Wavefront sensor lens mount 1416
BS2 Mount 1406
Camera Lens Mount 1408
Wavefront Sensor Mount 1410
Collimator Mount 1412
Polarizer mount 1414

7.3.1. Base Plate

Figure 14:
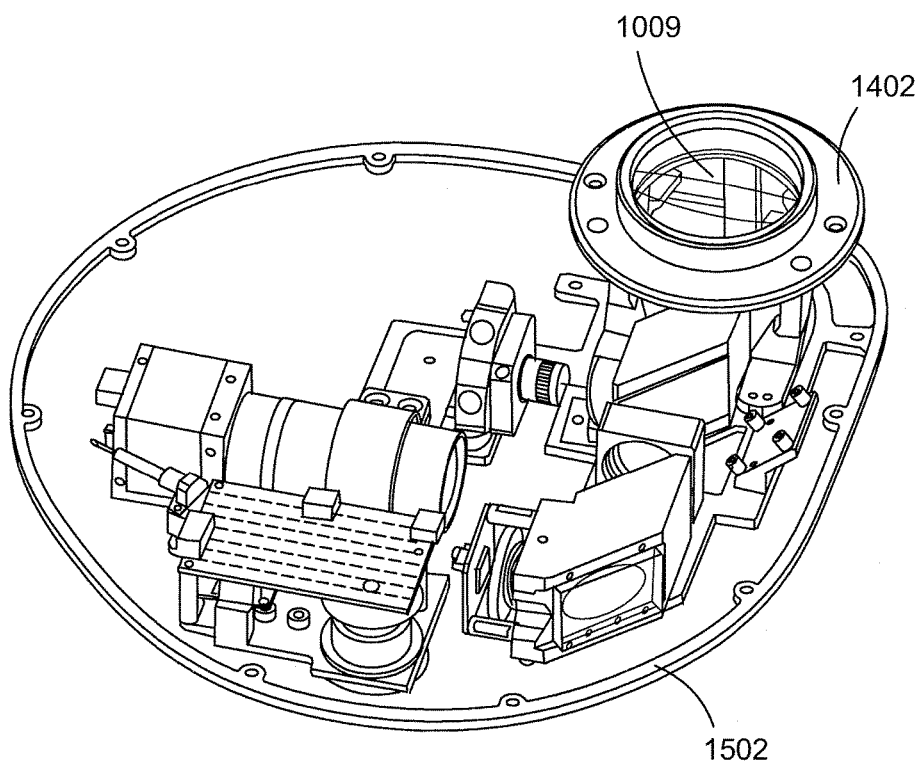
FIG. 14: shows a perspective view of the base plate with the mounted components shown in FIG. 13B.
Figure 15A:
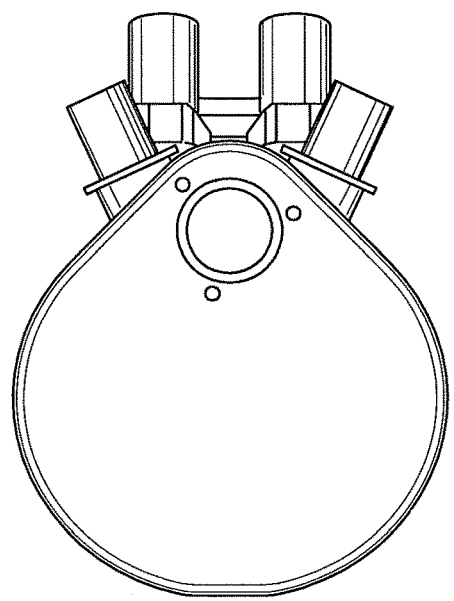
FIG. 15A: shows an intraoperative autorefractor mounted to an operation microscope.
Figure 15B:
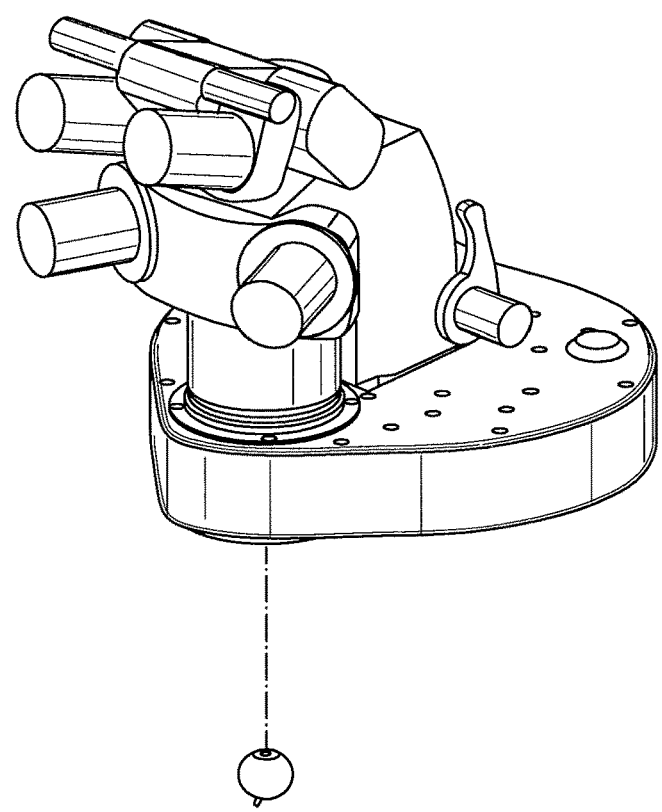
FIG. 15B: shows a perspective view of the intraoperative autorefractor mounted to an operation microscope.

The optical module 1002 is mounted to a base plate 1502 as shown in FIG. 14. The base plate serves the following purposes:

It provides a precise global registering and alignment reference for the haptic mounts so that optics are positioned precisely in space.
It provides a rigid structural frame for the mechanical positioning and fastening of internal components.
It constitutes part of the external enclosure of the device, as a mechanical and environmental barrier.
It outlines and determines the footprint of the device.
It provides a base to secure the bottom enclosure.
It contains supporting structures to mount electronic components, in particular the main electronics boards (e.g. interfaces 1006 and 1017, and SLD 53).

The mechanical design also includes an enclosure which is attached to the base plate.

7.3.2. Mounting of DM1 for Minimal Device Height

The mechanical design includes a special mount to hold the DM1 optical component 1020. DM1 1020 is a rectangular dichroic mirror mounted at 45 degrees. The size of DM1 must be large enough so that its outside edges are outside the field of view of the OPMI 1008 and so that it allows transmission of the OPMI illumination beams. These requirements make DM1 1020 the limiting component in terms of device height. The DM1 mount 1403 allows DM1 1020 to protrude through the base plate 1502 so as to minimize the height of the IAR 1000.

Figure 16:
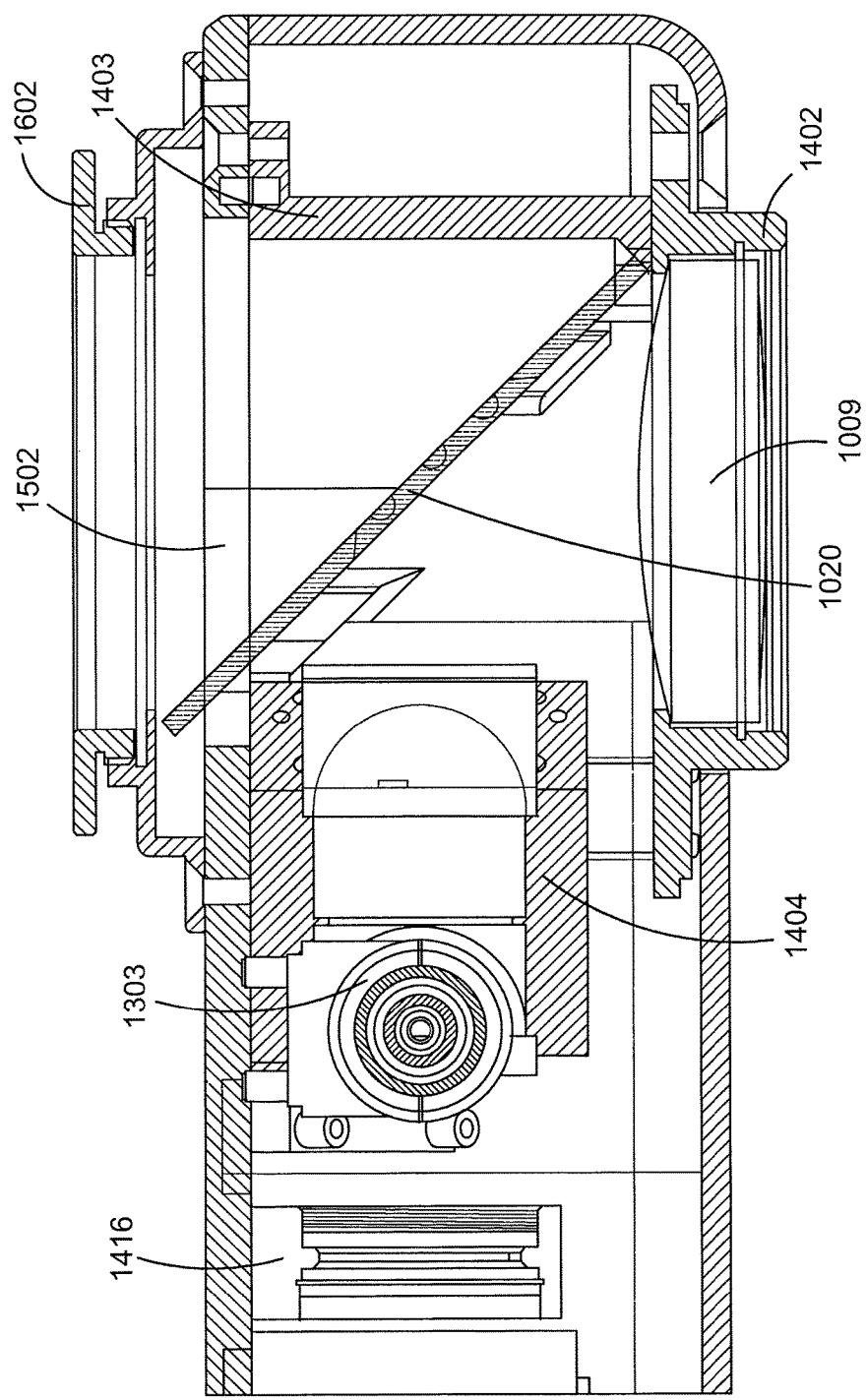
FIG. 16: shows a side view of the mounting of the refractor to the operation microscope.

In the cross-sectional image of FIG. 16, the top of DM1 1020 extends beyond the base plate 1502. DM1 1020 is guarded from outside contact by the fixed ring 1602. This mounting scheme reduces the overall height of the device, as compared to placing DM1 1020 entirely under the base plate 1502. It also brings the optical axis of the IAR 1000 closer to the base plate 1502, allowing for shorter mounts and overall reduction/optimization of weight and height.

7.3.3. Mounting Of DM1 at an Angle

DM1 is positioned so that the main optical axis of the IAR 1000 is at 45 degrees from the central sagittal plane of the OPMI 1008. The advantages of this configuration are:

It provides even component distribution to both sides of the OPMI sagittal plane. This layout helps make the device symmetric. If DM1 1020 were in-plane with the OPMI 1008, the device would protrude significantly to one side. Protrusion could interfere with the function of OPMI accessories, such as the assistant scope.

It separates optical and mechanical mounting planes, reducing the risk of interference of their features.

8. Focal Length and System Length

Figure 17:
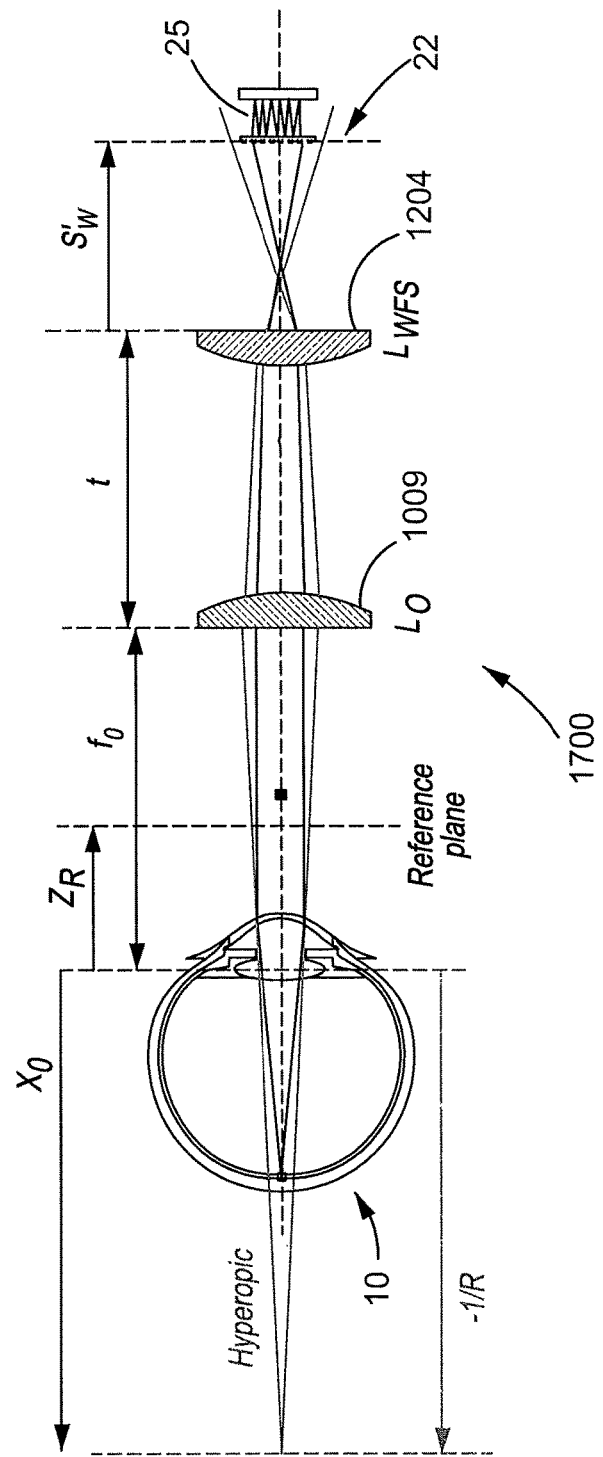
FIG. 17: shows a reduced schematic of the operation microscope mounted ophthalmic refractor of FIG. 10.

A reduced schematic 1700 of the system showing only the return path of the refractor beam is shown in FIG. 17. The focal length $f_0$ of lens 1009 is fixed. In this example the distance (t) between the two lenses is fixed. With these constraints, there is only one possible value of the focal length of the wavefront sensor lens 1204 which produces an image of the reference plane on the lenslet array 25 with a magnification m=−1. The expression of the focal length can be derived as follows.

With the notation of FIG. 17, the position and magnification of the primary image of the reference plane created by the objective lens 1009 are given by:

$$x'_o = -\frac{f_0^2}{z_R}. \qquad \text{equation 41}$$

$$m_0 = \frac{f_0}{z_R}. \qquad \text{equation 42}$$

To produce a total magnification $m=m_o \times m_w=-1$, the wavefront sensor lens must therefore produce a final image with a magnification of:

$$m_w = -\frac{z_R}{f_0}. \qquad \text{equation 43}$$

The magnification of the image produced by the wavefront sensor lens is:

$$m_w = \frac{f_w}{x_w}. \quad \text{equation 44}$$

Where $x_w$ is the distance between the first focal point of the wavefront sensor lens and the primary image:

$$x_w = f_w - t + f_0 \cdot \left(1 - \frac{f_0}{z_R}\right). \quad \text{equation 45}$$

Combining equations 43, 44 and 45 gives:

$$f_w = \frac{f_0^2 - (f_0 - t) \cdot z_R}{f_0 + z_R}. \quad \text{equation 46}$$

Figure 18:
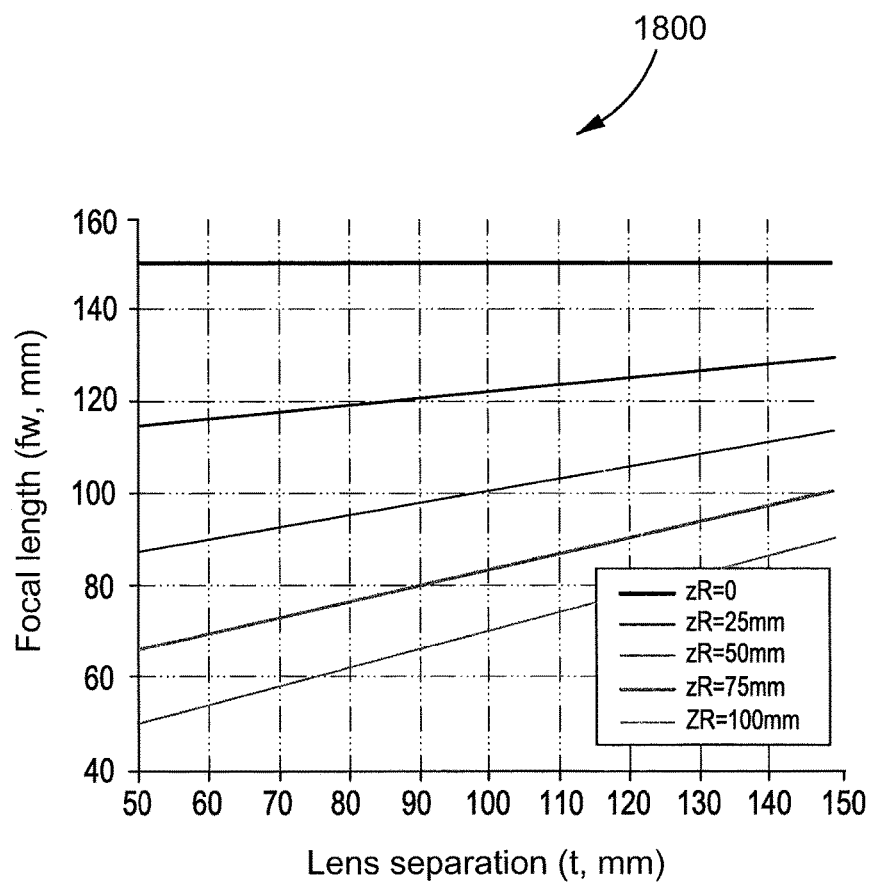
FIG. 18: shows a graph of the focal length of the wavefront sensor lens of the refractor in FIGS. 12 and 17 as a function of the separation between the objective lens and the wavefront sensor lens.

FIG. 18 shows a graph 1800 of the value of $f_w$ as a function of the separation (t) between the two lenses assuming a microscope with f=150 mm objective, for values of the reference plane position $Z_R$ ranging from 0 to 100 mm and resulting in decreasing focal lengths as $Z_R$ increases. For $Z_R>0$ the gradient of the straight-line curves shown are progressively more positive.

Figure 19:
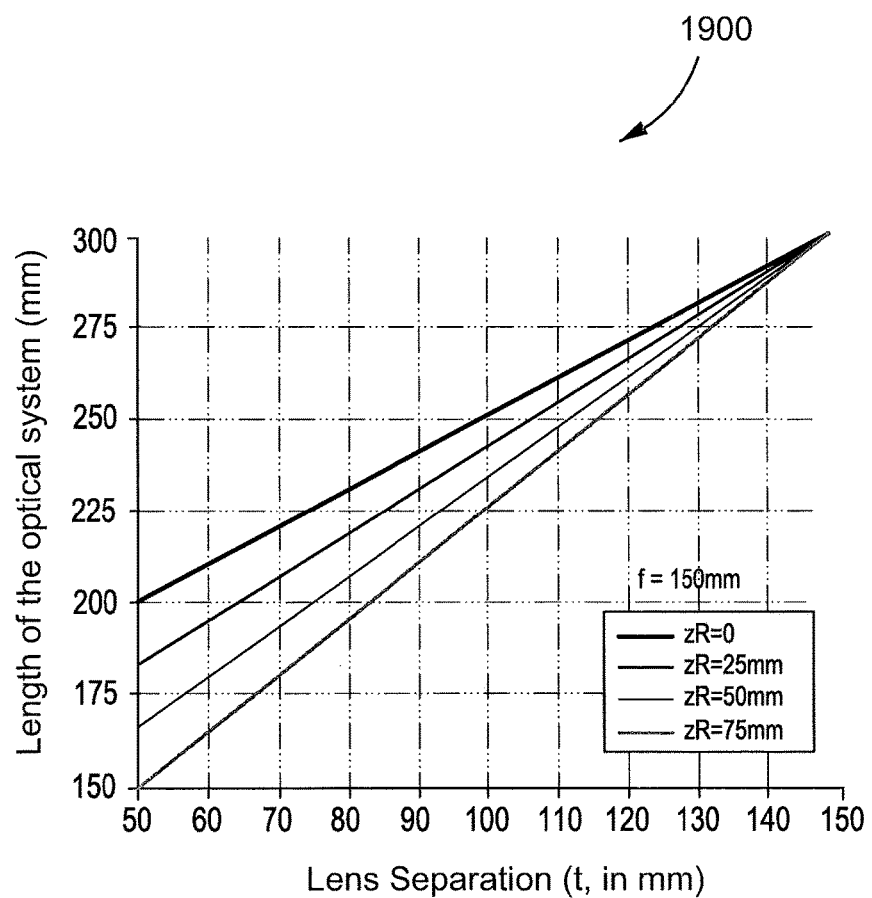
FIG. 19 shows the length of the optical system of FIGS. 12 and 17 as a function of the separation between the two lenses.

FIG. 19 shows a graph 1900 of the length of the system as a function of lens separation for different values of the reference plane position, according to equation 47 below. The total length of the system can be expected to range from 150 mm to 300 mm, depending on the lens separation and reference plane position. Values of the reference plane position $Z_R$ ranging from 0 to 75 mm result in decreasing length of the optical system as $Z_R$ increases. The gradient of the straight-line curves shown are progressively more positive as $Z_R$ increases. When the lens separation is equal to the focal length of the microscope, the length of the system is twice the focal length, or 300 mm for a microscope with focal length 150 mm.

$$L = f_0 - z_R + t \cdot \left(1 + \frac{z_R}{f_0}\right). \quad \text{equation 47}$$

In practice, the minimal lens separation is determined by the path length through the dichroic beam splitter DM1 1020 mounted in the microscope (approximately 35 mm) and the space needed to mount the dichroic mirror DM2 1021 for the OCT beam and the beam splitter BS 1022 for the refractor light source 53. The minimal lens separation is on the order of t=75 mm. With this value of t, the total length of the system will be on the order of 200 mm.

9. Relation Between Spherical Power and Refraction

The relation between spherical power measured by the lenslet array and refraction is provided by equation 48:

$$S = \frac{1}{\frac{f_w^2}{f_0 + f_w - t + R \cdot f_0^2} - \frac{f_w^2}{f_0 + f_w - t - \frac{f_0^2}{z_R}}}. \quad \text{equation 48}$$

Which can be written:

$$S = -\frac{1}{1 + R \cdot z_R} \cdot \left[\frac{1}{f_w} + \frac{1}{f_0} - \frac{t}{f_w \cdot f_0} + R \cdot \frac{f_o}{f_w}\right] \cdot \left[\left(\frac{1}{f_w} + \frac{1}{f_0} - \frac{t}{f_w \cdot f_0}\right) \cdot z_R - \frac{f_o}{f_w}\right]. \quad \text{equation 49}$$

Or:

$$S = \frac{1}{1 + R \cdot z_R} \cdot \left(P_L + R \cdot \frac{f_o}{f_w}\right) \cdot \left(\frac{f_o}{f_w} - P_L \cdot z_R\right). \quad \text{equation 50}$$

Where $P_L$ is the effective power of the relay system. Now, from equation 46, we have $$\frac{f_o}{f_w} = \frac{f_o \cdot (z_R + f_o)}{f_o^2 - z_R \cdot (f_o - t)}. \quad \text{equation 51}$$

$$P_L = \frac{2f_o - t}{f_o^2 - z_R \cdot (f_o - t)}. \quad \text{equation 52}$$

Combining equations 52, 53 and 54, gives:

$$S = \frac{1}{f_o^2 - z_R \cdot (f_o - t)} \cdot \frac{(2f_o - t) + R \cdot f_o \cdot (z_R + f_o)}{1 + R \cdot z_R}. \quad \text{equation 53a}$$

or, in terms of $f_w$:

$$S = \frac{f_o}{f_w} \cdot \frac{\frac{2f_o - t}{f_o \cdot (z_R + f_o)} + R}{1 + R \cdot z_R}. \quad \text{equation 53b}$$

equation 53 can be solved to find the expression of the refractive error as a function of measured spherical power (calibration equation):

$$R = -\frac{(2f_o - t) - (f_o^2 - z_R \cdot (f_o - t)) \cdot S}{f_o \cdot (z_R + f_o) - (f_o^2 - z_R \cdot (f_o - t)) \cdot z_R \cdot S}. \quad \text{equation 54a}$$

$$R = -\frac{\frac{2f_o - t}{f_o \cdot (z_R + f_o)} - \frac{f_w}{f_o} \cdot S}{1 - \frac{f_w}{f_o} \cdot z_R \cdot S}. \quad \text{equation 54b}$$

The general relationship between spherical power and refractive error is similar to the one produced with the original design (outside-coupled). The non-linearity of the response increases as the reference plane moves further away from the cornea. When the separation between the objective lens 1009 and wavefront lens 1204 increases, the spherical power decreases.

The range of myopia that can be measured is determined by the singularities in equation 53b. The singularity occurs when the denominator is equal to zero, or:

$$R = -\frac{1}{z_R}. \quad \text{equation 55}$$

When $R<-1/Z_R$, the measured spherical power becomes positive. The values of the spherical power in patients with very high myopic errors could be interpreted as a hyperopic error. To avoid this problem, a value of $Z_R$ equal to 50 mm or less may be used. With $Z_R=50$ mm, the theoretical myopic range is −20D and confusion between myopia and hyperopia can only occur in patients with myopia larger than −20D. In practice, the true myopic range will be smaller than the theoretical value predicted using equation 56, because of the limited dynamic range of the wavefront sensor.

There are no significant differences in the theoretical performance between the designs of Example 1 and Example 2 (inside-coupled instead of outside-coupled). In the outside-coupled design, the myopia range increases when the reference plane is closer to the cornea. Also, the effect of focusing errors on the precision of the measurements decreases as the lens separation decreases.

The following parameters provide an acceptable trade-off between accuracy, range, and length of the system:

25 mm<$Z_R$<50 mm
75 mm<t<100 mm

The corresponding values of the focal length of the wavefront lens 1204 are provided in the table below, assuming a microscope with a focal length fo=150 mm.

TABLE 3

Focal lengths for different distance and reference plane values

|  | $z_R$ = 25 mm | $z_R$ = 50 mm |
|---|---|---|
| t = 75 mm | 118 mm | 94 mm |
| t = 100 mm | 121 mm | 100 mm |

10. Ophthalmic Surgical Procedures

The embodiments of refractor described above may have particular utility during an ophthalmic surgical procedure. The ophthalmic surgical procedure may, for example, be any surgery affecting the refractive state of the eye, including cataract surgery, lens refilling surgery or corneal refractive surgery. During these surgical procedures, it may be beneficial for the surgeon to have access to a measurement of the refractive state of the patient. It may be even more beneficial for the surgeon to have access to a real-time measurement of the refractive state of the patient. It may be even more beneficial if the refractive state of the patient could be measured without having to move an operation microscope out of position.

Figure 20:
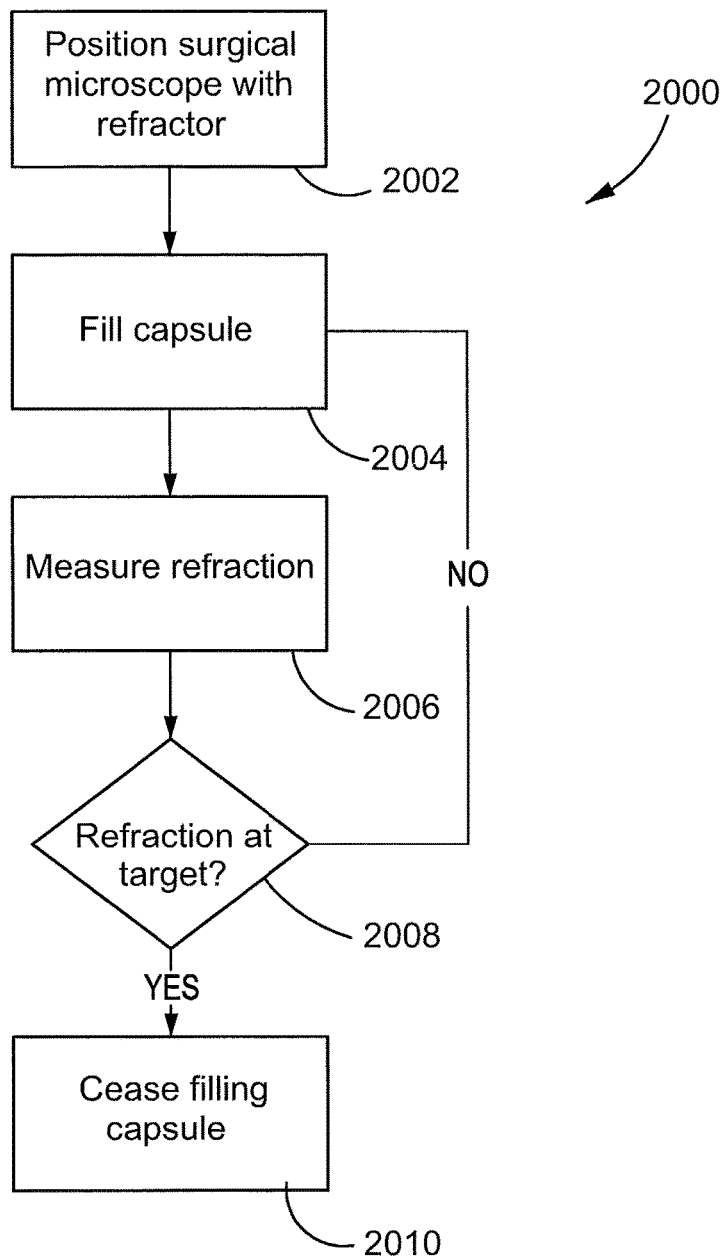
FIG. 20 shows a flow diagram of a surgical procedure utilising an operation microscope ophthalmic refractor.

FIG. 20 shows an example of a method 2000 of performing an ophthalmic surgical procedure. The example procedure is filling or refilling of a lens in the form of an intra-ocular lens inserted after removal of a cataract. The method includes utilising any one of the embodiments of refractor described herein above. In the particular embodiment described, the refractor is an operation microscope mounted refractor, as generally described with reference to FIG. 9. However, in other embodiments, the refractor may be free-standing or hand-held.

In step 2002, the surgical microscope 901 is positioned over the patient's eye. The surgeon may have inserted or accessed the intraocular lens with the surgical microscope in this position. The surgeon then prepares to fill or refill the lens so as to achieve a required refractive state of the eye. This includes, for an outside-coupled design, placing the beam splitter 916 in position below the entrance lens 921. The refractor is on so as to constantly measure the refraction from the subject eye. In step 2004 the lens is filled, which affects the refractive state of the eye, which is measured in step 2006 and the results provided to the surgeon. The surgeon can then decide, in step 2008, whether the target refractive state has been reached and if not fill the lens a different amount until the target is reached. Once the target is reached, the surgeon ceases filling the lens capsule (step 2010) and may continue with the surgery, for example closing the lens capsule and the cornea.

It will be appreciated from the example given above, that a similar feedback arrangement can be provided for the other types of surgery that affect the refractive state of the eye.

Although the embodiments of refractor described above are non-linear, so as to provide a useful dynamic range, the refractors still have a useful sensitivity about emmetropia, which is typically the target of the ophthalmic surgeon. Accordingly, from one perspective embodiments of the refractor described above may provide a useful balance of working distance, dynamic range and sensitivity.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for measuring ophthalmic refractive error, the method comprising:
   i) utilizing a relay system to image a wavefront of a return light beam from an eye of a subject by directing the wavefront of the return light beam onto a Hartmann-Shack sensor system positioned at a location in front of the cornea, wherein:
      a) the relay system comprises a first plano-convex lens and a second plano-convex lens placed about a lens plane ($Z_L$) positioned between the cornea and the sensor plane defined by the Hartmann-Shack sensor system to position a reference plane ($Z_R$) anterior to the cornea; and
      b) at least one of the relay system and the Hartmann-Shack sensor are configured so as to provide a non-linear relationship between spherical power and refractive error; and
   ii) utilizing a computational system to receive from the Hartmann-Shack sensor system a spot distribution and compute a value indicative of the refractive error.

2. The method of claim 1, wherein utilizing the computational system to receive from the Hartmann-Shack sensor system a spot distribution and compute a value indicative of the refractive error comprises utilizing the computation system to compensate for said non-linear relationship.

3. The method of claim 1 further comprising one of continuously or intermittently repeating said processes of utilizing a relay system and utilizing a computational system.

4. The method of claim 1, wherein the first plano-convex lens and the second plano-convex lens are separated by a distance (t) in the range of 75 mm to 100 mm.

5. The method of claim 4, wherein utilizing the computational system to receive from the Hartmann-Shack sensor system a spot distribution and compute a value indicative of the refractive error comprises utilizing the computation system to compensate for said non-linear relationship.

6. The method of claim 5 further comprising one of continuously or intermittently repeating said processes of utilizing a relay system and utilizing a computational system.

7. A method of analyzing wavefront data, the method comprising:
  i) utilizing a relay system to image a wavefront of a return light beam from an eye of a subject by directing the wavefront of the return light beam onto a Hartmann-Shack sensor system positioned at a location in front of the cornea wherein the relay system comprises a first plano-convex lens and a second plano-convex lens placed about a lens plane ($Z_L$) positioned between the cornea and the sensor plane defined by the Hartmann-Shack sensor system to position a reference plane ($Z_R$) anterior to the cornea;
  ii) performing linear regression on centroid positions of spots defined by the wavefront data in at least two different directions to compute a slope value for each said direction; and
  iii) utilizing the computed slope values to compute and output a value for at least one of the group comprising mean spherical power (M), astigmatic power ($J_0$) and astigmatic power ($J_{45}$) vectors for the subject eye.

8. The method of claim 7, wherein utilizing the computed slope values comprises solving a set of simultaneous equations comprising as variables the slope values and M, $J_0$ and $J_{45}$ vectors.

9. The method of claim 7 further comprising:
  running an error minimization algorithm to find coefficients of a function defining the difference in position between centroids of spots defined by the wavefront data and reference centroid positions, wherein the reference centroid positions compensate for any non-linear relationship and wherein the coefficients are defined so as to have a known mathematical relationship to said M, $J_0$ and $J_{45}$ vectors.

10. The method of claim 7 further comprising:
  computing a frequency domain transformation of the wavefront data; and
  computing the frequency of at least one centroid of the transformed wavefront data.

11. The method of claim 7, wherein the first plano-convex lens and the second plano-convex lens are separated by a distance (t) in the range of 75 mm to 100 mm.

12. The method of claim 11, wherein utilizing the computed slope values comprises solving a set of simultaneous equations comprising as variables the slope values and M, $J_0$ and $J_{45}$ vectors.

13. The method of claim 12 further comprising:
  running an error minimization algorithm to find coefficients of a function defining the difference in position between centroids of spots defined by the wavefront data and reference centroid positions, wherein the reference centroid positions compensate for any non-linear relationship and wherein the coefficients are defined so as to have a known mathematical relationship to said M, $J_0$ and $J_{45}$ vectors.

14. The method of claim 13 further comprising:
  computing a frequency domain transformation of the wavefront data; and
  computing the frequency of at least one centroid of the transformed wavefront data.

15. A method of performing an ophthalmic surgical procedure on a subject eye with a retina, the method comprising:
  i) illuminating a spot on the retina with a beam of light;
  ii) positioning an ophthalmic refractor to receive a return beam of light resulting from said illuminating;
  iii) reviewing an output from the ophthalmic refractor indicating the refractive error of the subject eye; and
  iv) responsive to said output, operating on said subject eye to achieve a target refractive error;
wherein said ophthalmic refractor comprises:
  a) a sensor system comprising a lenslet array and a light detector, the lenslet array focusing light onto the light detector; and
  b) a relay lens system disposed along an optical path of the return beam of light between the sensor system and a location for the anterior cornea of a subject eye, the relay lens system comprising a first plano-convex relay lens and a second plano-convex relay lens placed about a lens plane ($Z_L$) positioned between the retina and the sensor system to position a reference plane ($Z_R$) anterior to the cornea and imaging a reference plane onto the lenslet array; wherein the first plano-convex relay lens and the second plano-convex relay lens are positioned and have a focal length so that the reference plane ($Z_R$) is located in front of the cornea of the subject eye.

16. The method of claim 15, wherein the ophthalmic surgical procedure is selected from the group comprising: cataract surgery, lens refilling surgery or corneal refractive surgery.

17. The method of claim 15, wherein the first plano-convex lens and the second plano-convex lens are separated by a distance (t) in the range of 75 mm to 100 mm.

18. The method of claim 17 wherein the ophthalmic surgical procedure is selected from the group comprising: cataract surgery, lens refilling surgery or corneal refractive surgery.

19. The method of claim 15, wherein focal lengths (f) of the first plano-convex relay lens and the second plano-convex relay lens are equvalent.

20. The method of claim 15, wherein focal lengths (f) of the first plano-convex relay lens and the second plano-convex relay lens are mismatched.

* * * * *